(12) United States Patent
Pidgeon et al.

(10) Patent No.: US 6,641,783 B1
(45) Date of Patent: Nov. 4, 2003

(54) CHROMATOGRAPHIC SYSTEMS WITH PRE-DETECTOR ELUENT SWITCHING

(76) Inventors: Charles Pidgeon, 515 Evergreen St., West Lafayette, IN (US) 47906; Jianming Yin, 1848 Commonwealth Ave., Apt. 45, Brighton, MA (US) 02135; Nadege Rooke, 1620 Worcester Rd., Apt. 446B, Framingham, MA (US) 01702; Sonyuan Lin, 6 Great Rock Cir., Natick, MA (US) 01760; Jeffrey Giles, 347 Sprague St., Dedham, MA (US) 02026

( * ) Notice: Subject to any disclaimer, the term of this patent is extended or adjusted under 35 U.S.C. 154(b) by 0 days.

(21) Appl. No.: 09/499,904

(22) Filed: Feb. 8, 2000

Related U.S. Application Data

(60) Provisional application No. 60/119,011, filed on Feb. 8, 1999.

(51) Int. Cl.[7] .................. G01N 30/02; G01N 15/06; G01N 33/00; G01N 33/48; G01N 35/00
(52) U.S. Cl. .................. 422/70; 422/68.1; 422/81; 422/82; 436/43; 210/656; 210/659
(58) Field of Search .................. 422/70, 82, 81, 422/68.1; 210/659, 656; 436/43

(56) References Cited

U.S. PATENT DOCUMENTS 4,931,498 A   6/1990   Pidgeon
5,630,943 A   5/1997   Grill
5,641,406 A   6/1997   Sarhaddar et al.
6,344,172 B1 * 2/2002  Afeyan et al. ................ 422/70

FOREIGN PATENT DOCUMENTS

WO    WO 99/10522    3/1999

OTHER PUBLICATIONS

Kassel, Daniel B. et al., "Developments of a Fully Automated Parallel HPLC/Mass Spectrometry System for the Analytical Characterization and Preparative Purification of Combinatorial Libraries", *Anal. Chem.*, 70:4380–4388 (1998).

Kassel, D.B. et al., "Automated analytical/preparative high-performance liquid chromatography–mass spectrometry system for the rapid characterization and purification of compound libraries", *J. Chromatogr.*, A 794: 3–13 (1998).

* cited by examiner

*Primary Examiner*—Jill Warden
*Assistant Examiner*—Brian Sines
(74) *Attorney, Agent, or Firm*—Barnes & Thornburg

(57) ABSTRACT

This invention relates to a high efficiency chromatographic system. More specifically, the present invention relates to a chromatographic system for determining the physicochemical properties of one or more compounds using at least two chromatographic units in eluent flow communication with one eluent analyzer via an intermediate eluent switch. The present chromatographic system allows determination of physicochemical properties through the use of multiple chromatographic units in communication with one eluent analyzer via an eluent switch.

21 Claims, 16 Drawing Sheets

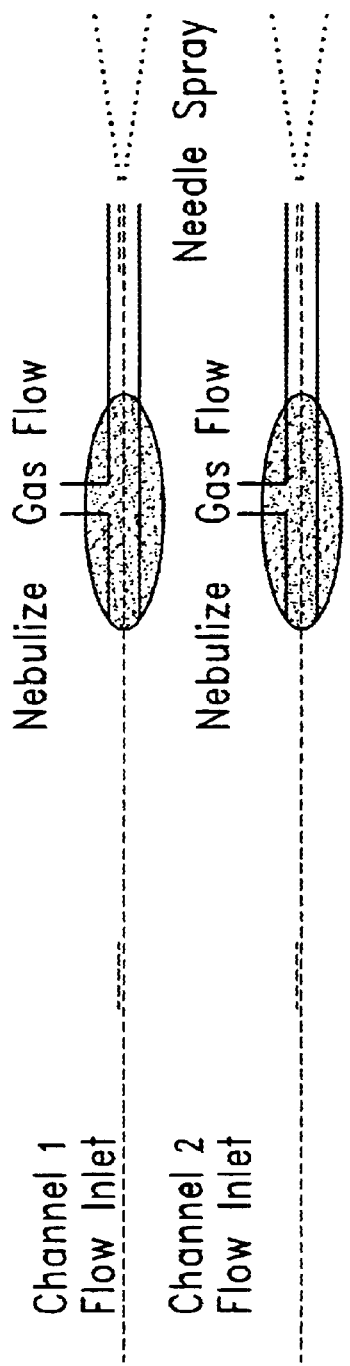
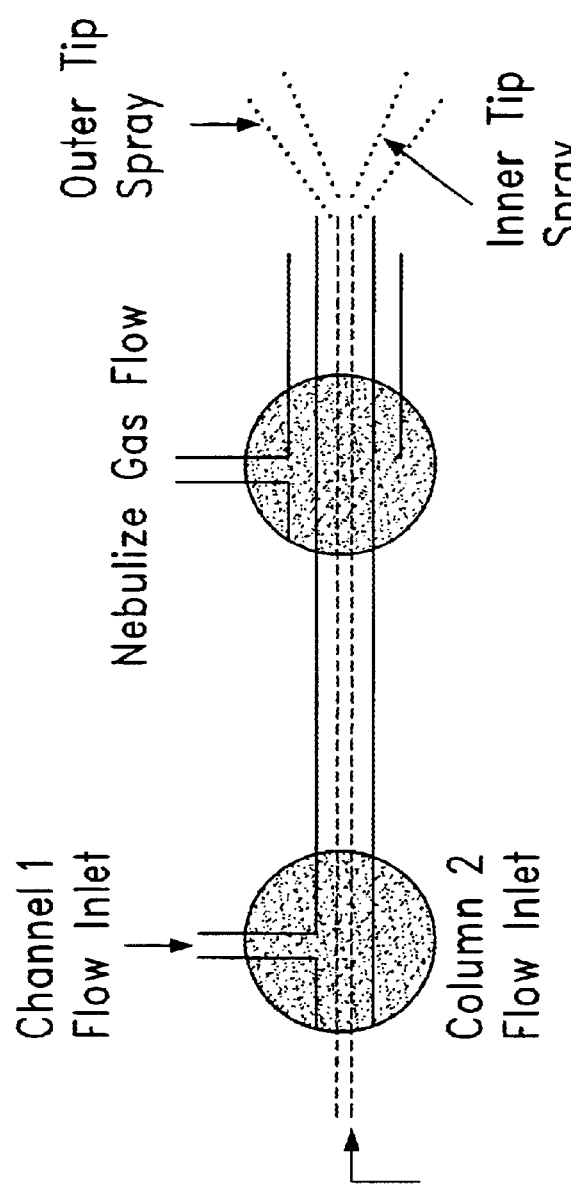
Fig. 4A
Fig. 4B

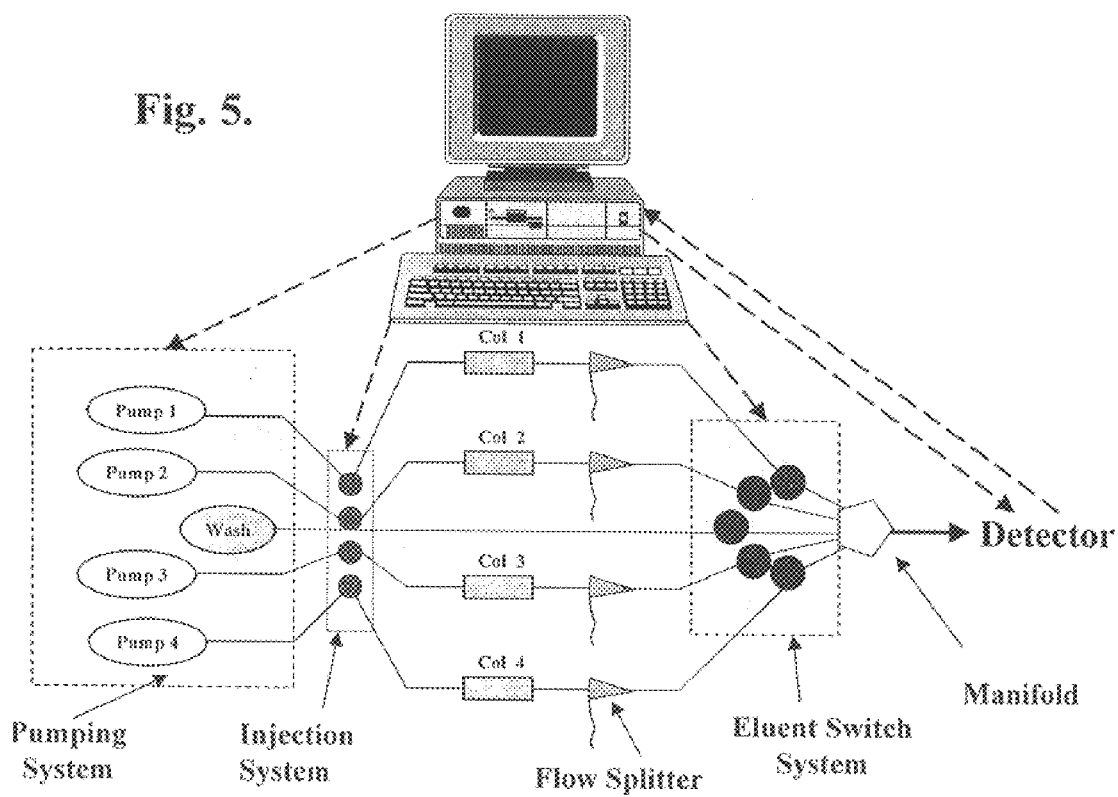

CHROMATOGRAPHIC SYSTEMS WITH PRE-DETECTOR ELUENT SWITCHING

This application claims the benefit of Provisional Application Ser. No. 60/119,011 filed Feb. 8, 1999.

FIELD OF THE INVENTION

This invention relates to a high efficiency chromatographic system. More specifically, the present invention relates to a chromatographic system for determining the physicochemical properties of one or more compounds using at least two chromatographic units in eluent flow communication with one eluent analyzer via an intermediate eluent switch.

BACKGROUND AND SUMMARY OF THE INVENTION

The emergence of automated chemical synthesis platforms coupled with combinatorial techniques as a routine tool in the pharmaceutical industry has enabled the synthesis of large numbers of molecules in a relatively short time. Millions of potential new drug candidates are created every year, and both pharmaceutical and biotechnology industries have embraced the challenge in recent years of developing new, faster and more efficient ways to screen pharmaceutical compounds in order to rapidly identify "hits" and develop them into promising lead candidates. This has created the need for high-throughput analytical approaches to characterize the synthesized compounds and has prompted the development of chromatographic systems specifically designed for the automated high-throughput identification, purity assessment or purification of combinatorial libraries.

Currently, automated, semi-quantitative assessment of combinatorial libraries is most readily accomplished by coupling HPLC with UV detection and mass spectrometry. Rapid HPLC methods with columns capable of delivering high-resolution separations have been developed in recent years, and have been well received by the drug discovery industry as a powerful tool particularly suited to handle the expanding analytical needs of combinatorial chemistry. The ability to characterize chemical libraries derived from combinatorial synthesis has in turn revealed that the purity of the compounds generated by this method is not necessarily high enough for biological evaluation of these compounds. Consequently, the scope of the high-throughput HPLC techniques initially designed and developed for structure confirmation purposes has expanded to include purity assessment and purification of the compound libraries to make them suitable for biological screening.

The technological advances directed toward the implementation of fast and high volume chromatographic systems have rapidly converged toward automated systems to accommodate the large number of compounds typically produced by most parallel syntheses nitially, automated preparative HPLC systems were designed so as to incorporate a fraction collection device activated upon detection of a threshold UV signal operating in conjunction with a secondary analytical unit (e.g., flow injection MS HPLC-ESI-MS) for the identification of the collected fractions. Recently, Kassel et al. (Zeng L., Burton L., Yung K., Shushan B., Kassel D. B., "Automated Analytical/ Preparative High-Performance Liquid Chromnatography-Mass Spectrometry System for the Rapid Characterization and Purification of Compound Libraries", *J. Chrom. A*, 794, 3–13, (1998)) added a major improvement to the technology by incorporating a "specific-mass-based" fraction collection device: fraction collection is initiated upon a real-time threshold reconstructed ion current signal being observed for a particular m/z input value, which corresponds to the mass of the compound being purified. This eliminates the need for post-purification screening and pooling required to identify the purified fractions of interest. Finally, they developed the system further and conceived an improved version of it ("Development of a Fully Automated HPLC/Mass Spectrometry System for the Analytical Characterization and Preparative Purification of Coinbinatorial Libraries", *Anal. Chem.*, 70(20), 4380–4388, (1998)). Kassel and coworkers devised an automated parallel analytical/preparative LC/MS system incorporating fast reversed-phase HPLC and electrospray ionization mass spectroscopy (ESI-MS), capable of processing the purification of two 96-well microtiter plates in parallel.

The system designed by Kassel et al. is comprised of two identical columns (analytical or preparative) running in parallel and is interfaced with two 96-well microtiter plates, each well containing a single synthetic product. Incorporation of a switching valve permits sequential loading of the samples onto the two columns: the autosampler draws the content of the first well of microtiter plate 1 and injects it onto the first column, then the autosampler picks up the content of the first well of microtiter plate 2 and loads it onto the second column. The same mobile phase is delivered to each column from a single HPLC pumping system, the flow from the pump splitting evenly between the columns (provided that the columns have comparable back pressures). Kassel et al. modified the IonSpray interface of the system to support flows from multiple columns and the eluents of the two columns were simultaneously introduced into the IonSpray source housing, and analyzed by mass spectrometry. This particular configuration allows the purification of chemical libraries based on mass spectrometry signal-detected fraction collection. Prior to performing the chromatographic separation, the mass and position of the expected products synthesized in the microtiter plate wells are specified. When a particular compound is detected by mass spectrometry in the course of the HPLC elution, the fraction collector connected to the column from which the compound is eluting is triggered, and the sample is collected in a specific tube determined by the position of the autosampler (for example, if the sample is drawn from well 1 of the autosampler/synthesis rack, the sample will be collected into tube 1 of the fraction collector rack). Thus, only compounds matching the molecular weight of the desired products are collected, and only one fraction is collected for each sample injected.

A major limitation of Kassel et al.'s parallel LC/MS technique is that the products to analyze must be of unique mass: false triggering of the fraction collectors is observed if two eluted compounds are of the same mass and similar ionization response. Thus, the synthesis of the combinatorial libraries must be carried out with the added restriction that no two expected products should yield the same molecular weight products. Further, for the flow to be equivalently transferred to the two columns requires that they have comparable back pressures because delivery of the solvent gradient is performed by a single pumping system. This generally requires that the columns be of the same size and be packed with the same chromatographic material. In addition, the design also dictates that both columns are eluted with identical mobile phase compositions. This limitation is usually of no consequence for the purification/ purity assessment of combinatorial libraries, since the synthesized compounds are generally structurally related and exhibit similar chromatographic behaviors.

The Kassel et al. system is particularly well suited for one of the major challenges found in the pharmaceutical industry: high-throughput structure confirmation and purity evaluation of large numbers of compounds derived from combinatorial syntheses. However, it does not address the other essential aspect of the drug discovery process: the physicochemical characterization of large numbers of compounds derived from parallel synthesis for quantitative structure-activity relationships (QSAR) studies, and the implementation of massive screening techniques for the biological evaluation of compound libraries.

Micromass© (Manchester, UK) implemented a multiplexed electrospray interface that is capable of sampling four individual liquid streams in rapid succession. The system comprises a single pump delivering solvent to all four columns run in parallel. The system has been integrated with the Z-Spray ion source of the Micromass© LCT orthogonal acceleration time-of-flight mass spectrometer. The inner source housing contains an array of four pneumatically assisted electrospray probe tips that are directed at the sampling cone. A hollow cylinder is positioned co-axially with the sampling cone. Two diametrically opposed circular apertures in the wall of the cylinder allow the spray from one electrospray probe tip to pass through the cylinder across the sampling cone, while all the other sprays are excluded. The spray from each probe tip is admitted in turn to the sampling cone as the cylinder is rotated by a programmable stepper motor. The source is supplied with a heated stream of dry nitrogen that facilitates the desolvation of ions in the selected stream. To monitor the four separate electrosprays, the rotor is rotated from position to position. An optical encoder indicates which spray channel is being sampled at any one time, and the data from that channel is written to its own specific data file. The system has recently been upgraded to include a total of 8 channels.

One of the disadvantages of this system is that is uses a single solvent delivery system for all the columns. Thus, the user is restricted to use column of identical size and packing material if the mobile phase flow is to be split equally through each column. In addition, the system utilizes a proprietary dual orthogonal "Z" sampling technique, which cannot be readily adapted to other mass spectrometers, much less to other types of detectors. Furthermore, mobile phase is continuously eluting from all the LC channels/probe tips in operation during any given run. The flow from the spray tips is never interrupted. The inner source cylinder functions essentially as a screen for all the sprays but one. The eluent from the sprays that are denied access to the MS capillary inlet thus hits the outside wall of the inner source cylinder. The stream of heated dry nitrogen gas facilitates evaporation of the solvent in the atmosphere. Although the maximum flow from each electrospray channel is small (100 $\mu$L/min) this potentially constitutes a health hazard, depending on the nature of the mobile phase or the analyte.

With the advent of combinatorial chemistry and the need to develop assays for the large numbers of compounds being made available using that technology, many researchers have focused their efforts on developing in vitro tests/assays that provide biologically significant compound information. Much work has been directed to the correlation of certain physicochemical properties with biological activity, both in the search for new therapeutic agents and in the understanding of compound toxicity from medicinal and environmental perspectives. For example, physicochemical properties of recognized significance to evaluation of a compound's biological activity are its lipophilicity, hydrophilicity, interfacial pKa, and membrane affinity, among others. The determination of these properties is critical for QSAR studies, and the worldwide discovery effort. The present invention relates to a system for determining not only chemical structure, but also the physicochemical properties critical for such QSAR studies and drug discovery efforts.

The chromatographic process represents a reversible equilibrium of solutes between the mobile phases and the stationary phases. The magnitude of solute retention is a direct result from this equilibrium and is typically expressed by a parameter, the capacity factor, $k'=(t_r-t_o)/t_o$ where $t_o$ is the dead time and $t_r$ is the retention time of the solutes. The capacity factor is therefore a stoichiometric mass distribution equilibrium of solutes between the mobile phases and the stationary phases, and its determination allows the calculation of various physicochemical values according to pre-determined algorithms.

The distinction between serial and parallel column chromatography is important. Serial column chromatography is an established method and involves automatically changing columns after a chromatographic run. This allows multiple columns to sequentially be evaluated. In contrast, parallel column chromatography allows multiple columns to simultaneously access one detector. Parallel chromatography has intrinsically higher throughput compared to serial chromatography.

Reducing the costs of analyzing large numbers of compounds is a commercial driving force for developing parallel chromatography systems. Chemical and biological studies that require the analysis of large numbers of samples have become routine for both drug discovery and drug analysis. Applications include routine chemical analysis, clinical trial samples, purification of compounds, obtaining physical or chemical parameters, measuring membrane binding properties, analyzing the quality of chemical libraries, natural product screening, chiral chromatography, etc.

These analysis problems are particularly amenable to parallel chromatography. For instance, high throughput screening of chemical libraries in drug discovery typically requires evaluation of thousands of samples. Similarly the analysis of biological samples from clinical trial studies can involve the analysis of large numbers of compounds and it is not uncommon to have >5000 samples for analysis in clinical trials.

The present invention finds application in chromatographic analyses of large numbers of compounds exhibiting actual or potential activity of biological or clinical significance. In such analyses, compounds are characterized and compared to compounds of known activity by their relative affinities to multiple stationary phases of biological significance, for example, using high performance liquid chromatography columns. Of particular use as stationary phases in such procedures are immobilized artificial membranes such as those described and claimed in U.S. Pat. No. 4,931,498. One approach to such analytical procedures is described and claimed in PCT patent application serial no. PCT/US98/17398, published Mar. 4, 1999, as WO99/10522, the content of which is incorporated herein by reference.

The present chromatographic system allows determination of physicochemical properties through the use of multiple chromatographic units in communication with one eluent analyzer via an eluent switch. The present invention dramatically increases the performance, efficiency, scope of use and commercial value of said chromatographic unit/ eluent analyzer system. The chromatographic unit can be any chromatographic system that can be interfaced with an analyzer or detector, and can include (but is not limited to)

high-performance liquid chromatography (HPLC) columns, capillary electrophoresis chromatography (CEC) columns, Gas Chromatography (GC) columns, super-critical fluid columns and microchips. The eluent analyzer unit is any instrument capable of identifying the presence, physico-chemical characteristics and/or chemical structure of a compound, including (but not limited to) a mass spectrometer (MS), a Fourier transform infra red spectrometer (FTIR), a Fourier transform ultra violet spectrometer (FTUV), standard UV detector, fluorescent detector, electrochemical detector, refractive index detector and a Fourier transform nuclear magnetic resonance spectrometer (FTNMR).

BRIEF DESCRIPTION OF THE DRAWINGS

FIG. 4 depicts Kassel's model for the simultaneous introduction of the column eluents into the electrospray source housing of a four-column HPLC/MS system.

FIG. 5 is a schematic diagram of a four-column High Throughput HPLC system equiped with an eluent switch device.

DETAILED DESCRIPTION OF THE INVENTION

Figure 1:
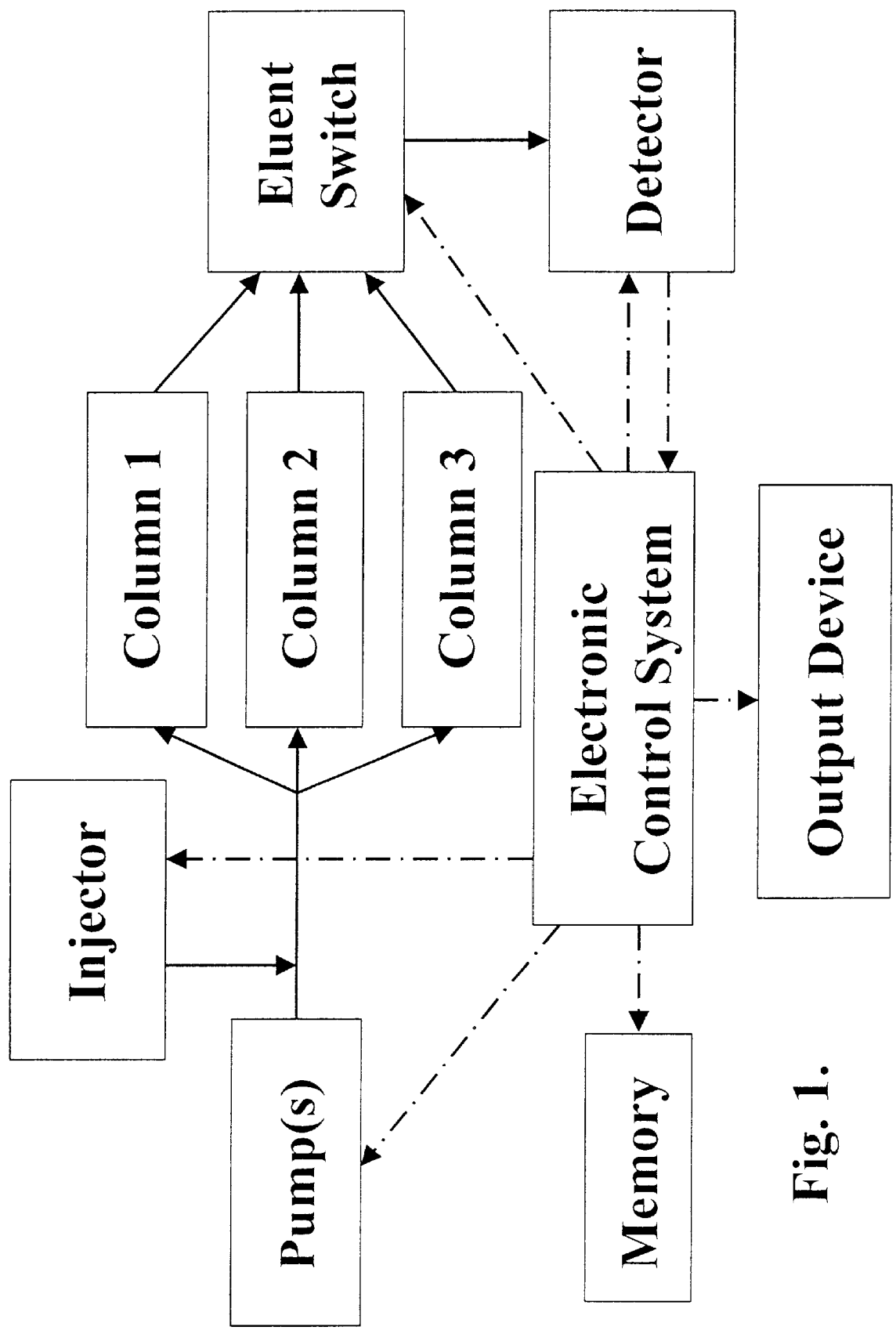
FIG. 1 depicts a diagram of one embodiment of the high-throughput chromatographic system described in this invention.

The present invention relates to a chromatographic system (and uses thereof) wherein more than one chromatographic unit is in fluid communication with an eluent switch and the eluent switch is in fluid communication with an eluent analyzer. The eluent switch is a valve-containing device capable of delivering small portions of the eluent from the individual chromatographic units to the eluent analyzer, typically in a sequential order. For purposes of the present invention, "valve" is defined as any of numerous mechanical devices by which the flow of liquid, gas, or loose material in bulk may be started, stopped, or regulated by a movable part that opens, shuts, or partially obstructs one or more ports or passageways; also: the movable part of any such a device.

The present design permits the simultaneous determination of the HPLC profiles (including structural identification) of a mixture of multiple compounds eluting from several independent chromatographic units operated in parallel. This technological advance allows a more efficient and cost-effective use of a costly eluent analyzer unit (such as, MS) by incorporating a simple and relatively inexpensive eluent switching device immediately upstream (eluent flowwise) from the eluent analyzer. For purposes of this invention, "eluent analyzer" and "detector" are synonymous.

In one apparatus embodiment, the present invention is directed to a chromatographic system comprising: at least two chromatographic units each having a sample compound loading system, a mobile phase entry port, an eluent exit port, and a stationary phase; a mobile phase supply system for delivering mobile phase to the mobile phase entry port of each chromatographic unit; a detector having an eluent sampling port, this detector capable of providing a signal of the presence or identity of an eluted sample compound in an eluent sample delivered to the sampling port; an eluent switch in eluent flow communication with each of the chromatographic units for delivering aliquots of eluent from each chromatographic unit sequentially to the eluent sampling port on the detector; and a data management device for receiving or storing signals from the detector.

The mobile phase supply system of this embodiment optionally includes a mobile phase pump for each chromatographic unit. In this embodiment, the pressure generated by said pumps can be constant or varied to control the flow rate of the mobile phase in each chromatographic unit. In another optional variation of this embodiment, the sample compound loading system of this embodiment comprises a valve that allows delivery of sample compounds and mobile phase into the chromatographic units when the valve is in one position and allows delivery of only mobile phase into the chromatographic units when the valve is in a second position.

In another apparatus embodiment, the present invention is directed to a system comprising: a fluid supply system; a compound loading system including multiple discreet chambers for receiving unique compound samples, said chambers in fluid flow communication with said fluid supply system; a detector having a sampling port, the detector capable of providing a signal of the presence or identity of a sample compound delivered to the sampling port; a sampling switch in fluid flow communication with the sample chambers and sampling port for delivering aliquots from each sample chamber sequentially to the sampling port on the detector; and a data management device for receiving or storing signals from the detector.

In an optional variation of this embodiment, the compound loading system of this embodiment comprises a valve or set of valves that allows delivery of sample compounds in one chamber when the valve system is in one position and allows delivery of a second sample compound in a second chamber when the valve system is in a second position. In another variation of this embodiment, the fluid supply system of this embodiment optionally includes a pump for each sample compound chamber.

In a variation of this embodiment, the sampling switch device contains a set of four valves (for a four-channel system) controlling the destination of the fluid flow from each respective chamber: toward the detector for analysis or to a waste container (or fraction collector). One valve of the sampling switch is in fluid communication with one individual sample compound chamber. After passing through the valve, the fluid from each chamber is delivered into a pre-detector manifold before entering the sampling port of the detector. The manifold includes a "wash solvent" inlet (controlled by another switch valve) allowing the introduction of a solvent mixture into the manifold after analysis of each sample. This minimizes sample carryover and systematic error due to contamination. If desired, when the detection system is a mass spectrometer, the wash solvent may contain a reference compound of known mass and ion current signal to facilitate data processing and interpretation: the mass spectral data obtained for the sample from each individual chamber would be separated by an identical signal corresponding to the reference compound in the wash solvent.

An example of application where such design finds use is the collection of flow injection data using a mass spectrometer. For instance, in a system comprising four channels, a different sample compound can be loaded in each chamber, the eluent switch would allow each sample compound to be analyzed sequentially by the mass spectrometer allowing the collection of mass spectral data for each of the four compounds. The valve configuration of the eluent switch would function as an indexing device. The system recognizes which channel is being sampled at any one time and the data management device produces a discrete data file for each compound. This system allows high throughput collection of mass spectral data by flow injection, for the purpose of analyzing, identifying, assessing the purity or building a reference library of mass spectral data for each of the sample compounds.

In another embodiment, the present invention is directed to a method of operating two or more chromatographic units in parallel using a single detector wherein the eluent from each of the chromatographic units is directed into an eluent switch adapted to deliver sequentially portions of the eluent from each of the chromatographic units comprising: applying the sample compounds into at least two chromatographic units each having a sample compound loading system, a mobile phase entry port, an eluent exit port, and a stationary phase; supplying mobile phase into the mobile phase entry port of each chromatographic unit using a mobile phase supply system; eluting the sample compounds from each of the chromatographic units into an eluent switch in eluent flow communication with each chromatographic unit; said eluent switch being capable of sequentially delivering aliquots of eluent from each chromatographic unit to a detector in eluent flow communication with the eluent switch; detecting the presence or identity of an eluted sample compound in an eluent portion delivered to the detector; generating a signal when such presence or identity of an eluted sample compound is detected; and receiving or storing such signal.

In optional variations of this embodiment, the application of sample compounds to the chromatographic units is accomplished by using an injector comprised of a valve and at least two sample loops wherein the injector valve, when placed in one position, allows delivery of the compounds into the sample loops and also allows the mobile phase to bypass the sample loops and be delivered into the chromatographic units; said sample valve, when placed in a second position, allows delivery of the compounds and mobile phase from the sample loops into the chromatographic units. Further, the step of detecting the presence or identity of an eluted compound is optionally accomplished by using a detector comprised of a mass spectrometer, a Fourier transform infra red spectrometer, a Fourier transform ultra violet spectrometer, or a Fourier transform nuclear magnetic resonance spectrometer. Other optional variants of this embodiment include the step of eluting the sample compounds using mobile phase supplied to at least two chromatographic units comprised of high performance liquid chromatography columns, gas chromatography columns, super-critical fluid columns, capillary electrophoresis columns or chromatographic microchips.

By allowing simultaneous chromatographic runs using more than one chromatographic unit (while only requiring one eluent analyzer), the present chromatographic system provides certain advantages when coupled with methods for determining physicochemical properties of one or more compounds in a test sample. In one embodiment, the present chromatographic system or method is used in conjunction with a method for separating and providing data characteristic of physicochemical properties of one or more compounds in a test sample. Such data can be derived from various peak characteristics such as retention time, the peak width at half height (peak width), the four moments (mean, variance, skewness and kurtosis); all of these peak characteristics may provide valuable data for evaluation and determination of physicochemical values of compounds. In one example of this embodiment, the present system is comprised of at least two chromatographic units, each comprising a stationary phase, a test sample loading port, a mobile phase entry port, and an eluent exit port; at least one mobile phase supply system for delivering mobile phase to the mobile phase entry port of the respective chromatographic units, an eluent analyzer capable of providing a signal of the presence or identity of a compound in an eluent portion; a programmable eluent switch for receiving eluent from each of the chromatographic units and delivering at least a portion of the eluent from each chromatographic unit to the eluent analyzer; and a data management system capable of receiving signals from the eluent analyzer and storing or recording said signals to provide a record of the time dependent elution of compounds from each chromatographic unit.

In this embodiment, the method for separating and providing data characteristic of physicochemical properties of one or more compounds in a test sample can be any one of a variety of methods used for such purposes. For example, the method (to be used in conjunction with the chromatographic system of the present invention) can be comprised of dissolving said compounds in a plurality of liquid media, each liquid medium having a predetermined composition, to form a multiplicity of test solutions of the set of compounds. Each test solution is then contacted with a surface under a pre-determined set of conditions of temperature and pressure. The surface is selected such that it exhibits a compound-dependent affinity for each compound. The affinity can be of a specific or non-specific nature. A parameter dependent on the affinity of the surface for each compound in each test solution is measured after contact of the solution with the surface under the pre-determined set of conditions. The measured parameters are then used to calculate the physicochemical value according to a pre-determined algorithm. Typically at least a portion of the compounds tested are compounds having a known value for the physicochemical characteristic being calculated. Preferably the method is implemented using liquid chromatography, more preferably high pressure liquid chromatography, to carry out the step of contacting each test solution with the surface. The stationary phase comprises the surface, the aqueous medium is the mobile phase, and the affinity-dependent parameter is the retention time for each compound.

One embodiment of this method (to be used in conjunction with the chromatographic system of the present invention) requires minimal experimental effort for the high throughput simultaneous determination of both $^{bulk}$pKa and $^{surface}$pKa of compounds. The method for determining pKa involves dissolving a set of compounds in a plurality of aqueous media, each having a unique pH to form a multiplicity of test solutions of said compounds (each also having unique pH). Each of the test solutions is then contacted with a chromatographic unit containing a surface exhibiting a compound-dependent affinity for the dissolved compounds, and then a parameter dependent upon the affinity of the surface in each solution for each of the compounds may be calculated after the compounds are evaluated by analysis of each solution after it is contacted with the surface. The dissociation constant for each compound is then calculated from the pH-dependent measured parameters for each respective compound.

The step of contacting each solution with the surface is carried out by liquid chromatography using a stationary phase and a liquid mobile phase wherein the stationary phase comprises the surface and the aqueous medium is the mobile phase. In such embodiments the test solutions having unique hydrogen ion concentrations are effectively formed in the chromatographic column with the aqueous medium mobile phase. The affinity-dependent parameter can be the retention time for each compound. The surface can be selected from a wide variety of commercially available chromatographic supports. One preferred class of surfaces is a membranous or membrane mimetic surface comprising phospholipids covalently bound to a solid substrate.

Chromatography will provide the capacity factors k' of each of the many compounds detected upon elution from the column, at (for example) various mobile phase pH's. Correlation of the capacity factors with the pH of the mobile phase allows the calculation of the $^{bulk}$pKa and $^{surface}$pKa for each compound. The chromatographic method is fast, convenient, and of wide scope, as it can by applied to any chromatographic substrate surfaces whether commercially available or custom designed. Further, use of the present multi-column chromatographic system employing a pre-detector eluent switch allows for simultaneous high-throughput analyses of a plurality of chemical compounds in a plurality of test media, thus increasing the rapidity and efficiency with which physicochemical properties can be determined for a large number of compounds. Access to the interfacial pKa of a wide variety of chemicals with numerous types of surfaces is therefore possible.

The present invention is useful for determining a suitable mobile phase/stationary phase combination for the analysis and/or purification of compounds. For example, one embodiment involves the use of four chromatographic units, each with a unique stationary phase, with the same mobile phase used in each chromatographic unit. A sample of test compound is injected into each chromatographic unit and the compounds are eluted. Portions of the eluent from each column are sequentially delivered to the detector via the eluent switch. The detector determines the presence of the compound and delivers a signal from which the elution profile of each respective column is determined. Upon analysis of this data, the best combination between the four stationary phases and the mobile phase used is determined. Optional variations of this embodiment include using the same stationary phase in the chromatographic units and varying the mobile phase used to elute each respective chromatographic unit, or varying both the stationary and mobile phases for each respective chromatographic unit. This analysis of stationary phase/mobile phase combinations can be performed on a large variety of compounds, including (but not limited to) chiral compounds, lipids, amino acids, sugars, nucleotides, etc. The present invention is a dramatic improvement over currently used techniques wherein a separate "run" is necessary for every combination of mobile phase and stationary phase tested.

The present invention greatly facilitates analysis of the properties of surfaces, such as (but not limited to) lipids, amphiphilic compounds, immobilized artificial membranes, etc. As one example, the surfaces used as stationary phase are varied for each respective chromatographic unit, while mobile phase, pressure and flow rate are the same for each. A test compound with known physicochemical properties is simultaneously injected into each chromatographic unit and eluted. Portions of the eluent from each column are sequentially delivered to the detector via the eluent switch. The detector determines the presence of the compound and delivers a signal from which the elution profile of each respective column is determined. Upon analysis of this data, conclusions concerning the interaction between the test compound and the various surfaces employed in the stationary phase are drawn. For example, the comparative non-specific binding of a known compound with various surfaces can be readily compared using the present invention.

In particular, when the chromatographic surfaces are membrane mimetic surfaces, the membrane affinity fingerprint (MAF) of said compound can be determined. Briefly, the membrane binding properties of test compounds can be calculated, or they can be determined empirically with use of, for example, liposomes, immobilized artificial membranes (such as those described in U.S. Pat. No. 4,931,498, the disclosure of which is incorporated herein by reference), Langmuir Blodget films, computer chips or similar devices with immobilized lipids, capillary zone electrophoresis columns coated with membrane lipids, and the like. In the case of immobilized artificial membranes (IAMs), the numerical values characteristic of membrane affinity are determined chromatographically using an aqueous mobile phase and a stationary phase comprising a membrane mimetic surface as defined in U.S. Pat. No. 4,931,498. Membrane binding properties of a set of test compounds of unknown biological activities are compared to the membrane binding properties of control compounds having known in vivo biological activity to assess the probability that the test compounds will exhibit one or more biological activities in vivo. For each control compound there is a defined and ordered set of numerical values characterizing a biologically relevant interaction (e.g., affinity) of that compound with each of the selected membrane mimetic surfaces.

The ordered set of numerical values for each control compound or each set of control compounds (i.e., a "training set") can be represented by the expression $<C_1, C_2, \ldots, C_n>$ wherein n is the number of membrane mimetic surfaces identified and used in the screening method. A similar ordered set of numerical values $<T_1, T_2, \ldots, T_n>$ for each test compound characteristic of its biological relevant interaction with each of the respective membrane mimetic surfaces is determined. The set of numerical values for each test compound is then compared with the set of respective values for the control compounds, and the biological properties of those control compounds having ordered sets of numerical values best matching the respective numerical values in the ordered set of values for the test compound are identified. Pattern matching using vector calculus, multivariate analysis or principal component analysis of the numerical values characteristic of the test compounds and the control compounds allows comparison of the membrane binding properties of the test compounds and each of the control compounds or, if the control compounds all have a common biological activity/property, average or mean membrane binding values of the set of control compounds for each membrane mimetic surface.

The invention also finds use in high throughput screening of complex mixtures of compounds for a predetermined chemical or biological property. Briefly, for any one compound, a set of chromatographic profiles run using different sets of separation parameters constitutes a "chromatographic fingerprint" unique to this compound, and the probability for any two compounds to have the same chromatographic fingerprint decreases dramatically (to become zero) as the number of chromatographic conditions used to establish said chromatographic fingerprint increases. The term separation parameter refers to chromatographic variables which control/affect the separation process. Such parameters include (but are not limited to) stationary phase, mobile phase composition, mobile phase flow rate and column size. Pattern matching of the "chromatographic fingerprints" of each individual compound of a compound mixture with that of a reference compound with a known chemical/biological property allows the screening of the compound mixture for said chemical/biological property.

The present chromatographic system can be used in a method of identifying one or more compounds having a predetermined characteristic in a complex compound mixture. For this use, the present system employs more than one chromatographic unit, each unit having a unique set of separation parameters, thus producing a unique series of separation parameter-dependent fractions.

In one example, the method for identifying one or more compounds having the predetermined characteristic (to be used in conjunction with the present chromatographic system) comprises subjecting the compound mixture to a separation process using a first set of compound separation parameters (associated with the first chromatographic unit) to at least partially separate the compounds in the mixture into a series of separation variable-dependent fractions (Fa) in the order $Fa_1, Fa_2, Fa_3, \ldots Fa_n$ wherein n is the number of fractions collected using the first set of separation variables, at least a portion of which fractions include one or more compounds of the compound mixture. In step (b), step (a) is repeated for another chromatographic unit that has a second unique set of separation parameters to produce a second series of separation parameter-dependent fractions (Fb) in the order $Fb_1, Fb_2, Fb_3, \ldots, Fb_m$ wherein m is the number of fractions collected using the second set of separation parameters. Thus, for each chromatographic unit used, a set of fractions is generated. Each of the qth fractions obtained using each set of separation parameters (wherein q is the respective order number of the fractions obtained using each set of separation parameters) is combined to provide combined qth fractions.

Spectral data is then obtained on a sample of each of said combined fractions, the data being characteristic of the compound or compounds in the combined fractions. Each combined fraction is analyzed to detect the presence of the predetermined chemical, physical or biological characteristic and identifying each of those combined fractions that exhibit the predetermined characteristic. From this, a comparison of the spectral data for each of the combined fractions exhibiting the predetermined characteristic to identify spectral data common to each of said combined fractions can be made, and the compound or compounds characterized by the spectral data common to the combined fractions exhibiting the predetermined characteristic in said combined fraction can be identified.

In another embodiment, compound analysis is performed on the eluted sample compounds to determine their chemical structure. For example, compounds with predetermined physicochemical properties can be identified using the present invention. The present invention provides an embodiment wherein a library of structurally related compounds is eluted from two or more chromatographic units. Aliquots of the eluent from each column are delivered to a detector capable of determining both the presence and the structural identity of the eluted compounds. The signals generated by this detector are evaluated, and elution profiles and/or other physicochemical properties of the eluted compounds are determined. In this manner, compounds with elution profiles matching the predetermined physicochemical properties desired are selected and identified.

Compound purification can be accomplished using the present invention. For example, multiple test compounds are eluted from two or more chromatographic units and aliquots of the eluent are delivered to the detector via the eluent switch, which is configured so that the "waste" (i.e., that portion not delivered to the detector) is collected in a fraction collector from each respective chromatographic unit. The fraction collectors are coordinated with the time of detection such that the appropriate fraction containing any detected compound can be identified. When a compound with predetermined physicochemical properties is identified, the appropriate fractions containing a purified form of the identified compound are retained from the fraction collector (s).

The invention also finds use in the analysis, identification and purification of compounds of widely variant activity, i.e., activities ranging from pharmaceutical utility to toxicity. For example, determination of physicochemical characteristics of biologically active compounds, biologically toxic compounds and environmental toxins such as pesticides, herbicides, etc., can be accomplished using the present invention.

Another embodiment of the present invention is directed to a chromatographic system wherein multi-column parallel liquid chromatography columns are coupled with a mass spectrometry-based detector, which can be applied to the high-throughput determination of physicochemical values of a set of compounds, such as those that form a chemical library, with concomitant structural identification of said compounds and minimal experimental effort. In one embodiment, the technique is implemented using liquid chromatography, for example high performance liquid chromatography, interfaced with a mass spectrometer as the detection device via an intermediate eluent switch. One potential design includes a set of four chromatographic columns individually connected to four separate pumping systems maintaining a constant flow rate compatible with the mass spectrometer inlet requirements (typically about 1.0 mL/min). Although a four-column system is exemplified herein, the design can be adapted to include more or less than four columns. The columns can be simultaneously loaded with the same test solution containing a set of compounds dissolved in a solvent mixture, and run in parallel at constant flow rates. Delivery of the mobile phase by four independent pumping systems is crucial if a constant predetermined eluent flow rate is to be run through each column which contains different packing materials, as required by the mass spectrometer interface. If a single pump was to deliver solvent to a set of columns such that they contain different packing material, the difference in back pressure exhibited by said columns would result in the mobile phase being unequally split (non-similar flow rates) onto the columns.

For any one column, the back pressure is generally a function of the length of the column, the particle size and shape of the chromatographic material, and the viscosity of the mobile phase. Therefore, unless strictly identical columns are used in the HPLC system, the use of four independent pumping systems is imperative to ensure constant flow rates throughout the columns.

The advantage of using dedicated pumps for each column, as opposed to a single pumping system delivering the mobile phase to all columns (or using no pump at all), is that it allows the control of the flow rates throughout the columns. A system using a single pump would require the implementation of additional hardware to compensate for the undetermined flow rates in each column. For example the individual flow rates would have to be measured, and the development of the software for data processing would require more effort to account for the fact that the analytes on each column would not elute under comparable conditions (uneven flow rates). In addition, flow dependent experiments would be impossible to run, and quality control would be significantly affected, since it would be difficult to determine the amount of sample actually loaded on each column. With a one pump/one column system however, control of the flow rate is ensured, and thus no correction for k' is necessary. Multiple flow rates can be tested, and quality control is maximized.

In one embodiment, the injection device is such that it allows loading of the test solution onto one, two, three or all four columns. The injection system may comprise four individual injectors (one per column), which are loaded manually, and are electronically controlled so that simultaneous or staggered injection of the sample on one, two, three or all four columns is possible. Alternatively, the injection device may contain two 13-port valves connected in series, with electronically controlled shut-off valves incorporated upstream from each of the four injection loops to allow the operator to select the number of columns to be used for a particular run: these valves can be set in an open or closed configuration to allow or prevent respectively the introduction of the sample solution in the corresponding loops. Thus, depending on the application and the purpose of the study, any number of columns (but typically ranging from one to four) may be used during any one elution cycle. This will be controlled by the operator through a computer software interfaced with the LC/MS system. In another embodiment, the injection system allows for the loading of one sample solution per column. For this particular purpose, a design similar to the injection system described by Kassel et al. can be implemented.

Various types of columns can be used with this system, whether differing in size (analytical or preparative), solvent compatibility, stationary phase or any other characteristic relevant to use as a chromatographic unit. For example, various covalently bound stationary phases can be used as the test surfaces: chromatographic material can be employed, whether commercially available (C18, C8, C4, chiral packing material or other available chromatographic material) or material specifically designed and developed for a particular application or investigation. One group of surfaces is so-called membrane mimetic surfaces. The term "membrane mimetic surface" refers to any surface bearing immobilized amphiphilic molecules (i.e., those having both lipophilic and hydrophilic portions) capable of exhibiting some affinity for or otherwise interacting with a solute (e.g., a test or control compound) in a fluid phase in contact with the surface. The term is intended to encompass a broad scope of commercially or non-commercially available stationary phases. Membrane mimetic surfaces include those described in U.S. Pat. No. 4,931,498, specifically incorporated herein by reference. The choice of the chromatographic material will essentially depend on the types of compounds to be analyzed, the type of application under consideration, as well as which type of surface/solute interactions are under investigation.

A mass spectrometer coupled to the chromatographic system ensures an accurate and efficient detection and identification of the compounds eluting from the chromatographic columns, although other types of detectors are possible. The analytes eluting from the columns will alternatively be introduced into the electrospray source housing with the help of a pre-detector valve system incorporated between the columns and the mass spectrometer electrospray chamber.

In one embodiment of the invention, the eluent switch device contains a set of four 4-port switch valves controlling the destination of the eluent: toward the mass spectrometer for analysis or to the waste container (or fraction collector). One valve of the eluent switch is in fluid communication with one individual chromatographic column, and after passing through the valve, the eluent from each column is transferred into a pre-detector manifold before entering the detection system. This manifold is also connected to a "wash solvent" outlet (controlled by another 4-port switch valve) allowing the introduction of a reference solvent mixture into the manifold after every column eluent analysis. This would minimize sample carryover and systematic error due to contamination. If desired, when the detection system is an MS, the wash solvent may contain a reference compound (R*) of known mass and ion current signal allowing easier data processing and interpretation: the mass spectral data obtained from each individual column would be separated by an identical signal corresponding to the reference compound.

In one embodiment, the pre-detector eluent switch device is electronically controlled and allows the operator to preset the time, sequence and/or volume parameters for the introduction of the eluent from the various columns to the eluent analyzer. For example, the analysis sequence can be set so that eluents from column 1, column 2, column 3 and column 4 alternatively enter the electrospray housing for 2–3 seconds at a time, with introduction of reference solvent in between analyses for sample carryover problem elimination. Thus, the eluting samples from each column are analyzed alternatively, according to a pre-determined sequence programmed by the operator through a computer software interfaced with the LC/MS system. Each fraction is analyzed and its composition determined, so that each compound identified (MS) is associated with a retention time (chromatography) and a capacity factor. The data is processed, sorted and stored as four independent data files. From each capacity factor, the calculation of various physicochemical values for each compound detected is performed according to pre-determined algorithms. An obvious advantage of the technique of this embodiment is that it interfaces four HPLC systems with a single mass spectrometer, and thus has the data analysis capacity of four single-column LC/MS instruments with one fourth of the cost for analyzer equipment along with dramatic increases in speed and efficiency of the chromatographic process.

In another embodiment of the invention, the mobile phase is delivered to each column by independent pumping systems. This ensures the control of a constant eluent flow rate through each column, regardless of their types and sizes, and allows the data analysis to be performed with maximum accuracy and quality at the mass spectrometer interface. The use of independent pumping devices also leaves the possibility of using different mobile phase compositions for the columns if desired.

For purposes of the present invention, "sample compound loading system" means any device, vessel or instrument operated manually, mechanically or electromechanically that is capable of receiving a sample compound and delivering it into a chromatographic unit. Examples of such sample compound loading system include (but are not limited to) both manual and programmable high performance liquid chromatography injector systems for single and multiple injections commonly used in chromatographic processes.

The mobile phase is supplied to the chromatographic units via a mobile phase supply system. For purposes of this invention, "mobile phase supply system" refers to any device, vessel or instrument operated manually, mechanically or electromechanically that is capable of supplying mobile phase to the chromatographic units. One common embodiment of such mobile phase supply systems currently in use are high performance liquid chromatography pumps.

The mobile phase enters the chromatographic units via a mobile phase entry port. "Mobile phase entry port" refers to the place of entry of a mobile phase into a chromatographic unit thereby allowing the mobile phase to contact the stationary phase of a chromatographic unit. After contacting the stationary phase, the eluent (i.e., the mobile phase and sample compound(s)) exits the chromatographic unit via the eluent exit port.

Various components used in various embodiments of the present invention are well suited to control via electronic control systems. Examples of such controllable components include the mobile phase supply system, the injector or sample compound loading system, the eluent switch, and the detector. Such electronic control is achievable for any of the components individually or may be used to coordinate the control of the components simultaneously. An example of such electronic control systems is a computer with software.

The detector or eluent analyzer of the present invention sends a signal in response to the presence of a sample compound. This signal is received or stored by a data management device, which either stores the signal in memory or transforms the signal into a readable form of data and sends the data to an output device. This data management system may be the same device as used to control the operation of the various components of the system (the electronic control system) or may be a separate, independent device from the electronic control system. Such data management control systems are known in the art.

As shown in FIG. 1, one embodiment of the proposed technology is based on a chromatographic system containing a pumping system, an injector, multiple columns (preferably four, although a higher number is possible) run in parallel, a pre-detector eluent switch module, and a detector which must be such that it allows identification and quantification of detected compounds alone or in mixtures with other compounds on a millisecond time scale. An HPLC is the preferred chromatographic support for this invention, although other chromatographic techniques are suitable for the purpose (e.g., CEC, microchips, GC). The preferred detection device is a mass spectrometer, although other detection systems, such as FTIR, FTUV and FTNMR detectors are acceptable. The use of a tandem mass spectrometer (MS/MS) may be required for more complex cases where the identification of the compounds eluting from the columns is not possible after a single mass spectrometric analysis. Chemometrics is used to analyze data derived from the technologic design described in this invention.

The injection system may allow sequential loading of sample solutions onto the columns (one column-one sample) or simultaneous injection of the same sample onto several columns (the number of columns to be used in a run is determined and set by the operator prior to starting the experiment via a computer software interfaced with the HPLC/MS system).

In one embodiment, the pumping system contains four individual pump systems delivering the mobile phases to the various columns independently. The columns may be identical or may vary in type (packing material) or in size (analytical or preparative). The eluent switch device includes a pre-detector manifold allowing sequential analysis of the eluents from the various columns with a single spray-needle, the analysis sequence being determined by a program entered by the operator.

Injection System

For the construction of the sample injector, several designs are possible, depending on whether the same sample is to be simultaneously injected onto all columns, or if the application of interest requires the injection of one sample per column. For the latter case, the use of one injector per column is certainly a possibility, although a single-injection-port system is preferable.

Zeng and Kassel (Anal. Chem. 70:4380–4388 (1998)) designed a seven-port valve and a six-port valve injection system that may be used or adapted for the present invention. The six-port valve could be assigned two different positions (position 0 or position 1) and the seven-port valve three positions (1, 5, and 6). With the six-port valve in position 0, the samples were loaded onto the two columns independently (the configuration of the seven-part valve (position 1 or 6) determined which column the sample was loaded onto). When the six-port valve was in configuration 1 and the seven-port valve in position 5, the solvent was delivered into the two columns simultaneously. There are several disadvantages in this construction: (1) The ends of the two sample loops are closed. Without an outlet for the sample loops it is very easy to generate air bubbles in the sample loop and not have constant filling and loading on the column. This could affect the performance of the HPLC system and result in the injection of an inaccurate amount of sample; (2) It is difficult to load different amounts of sample onto different columns.

Multi-Column Sample Injection System

An instrumental set-up featuring the use of dedicated injectors and pumps for each columns, is proposed as shown in FIG. 5. Thus, the four columns would be connected to their corresponding injector and pump as in normal operation of HPLC. These sample injectors should be electronically operated, which ensures the injection being conducted simultaneously. Having electronic control of the injection valves would also allow the user to program the multiple injections at different time intervals (staggered instead of simultaneous), should such an experimental design be required.

Figure 2:
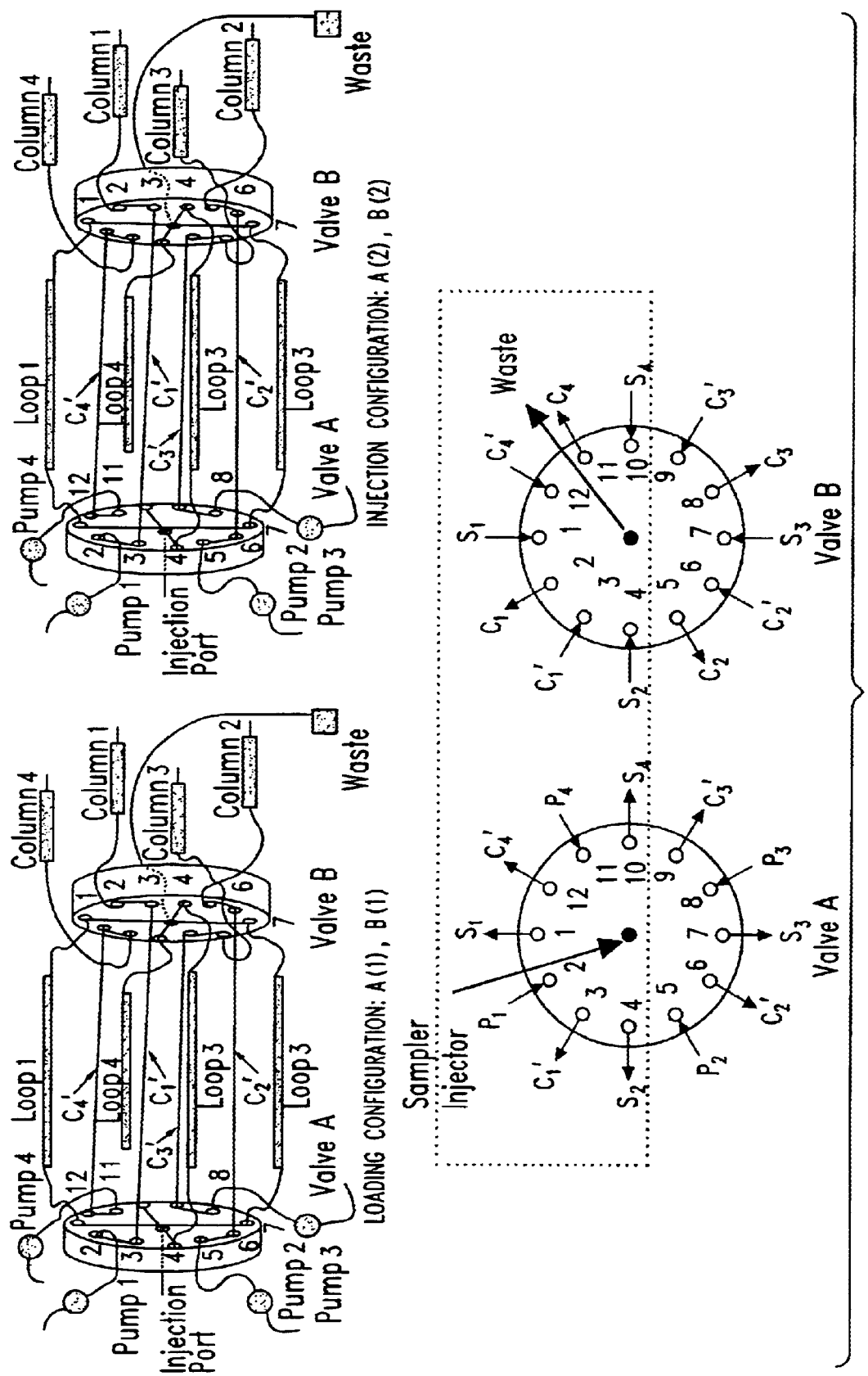
FIG. 2 depicts the hardware requirements and associated connections of the two 13-port valves contained within one embodiment of the injection system.
Figure 3:
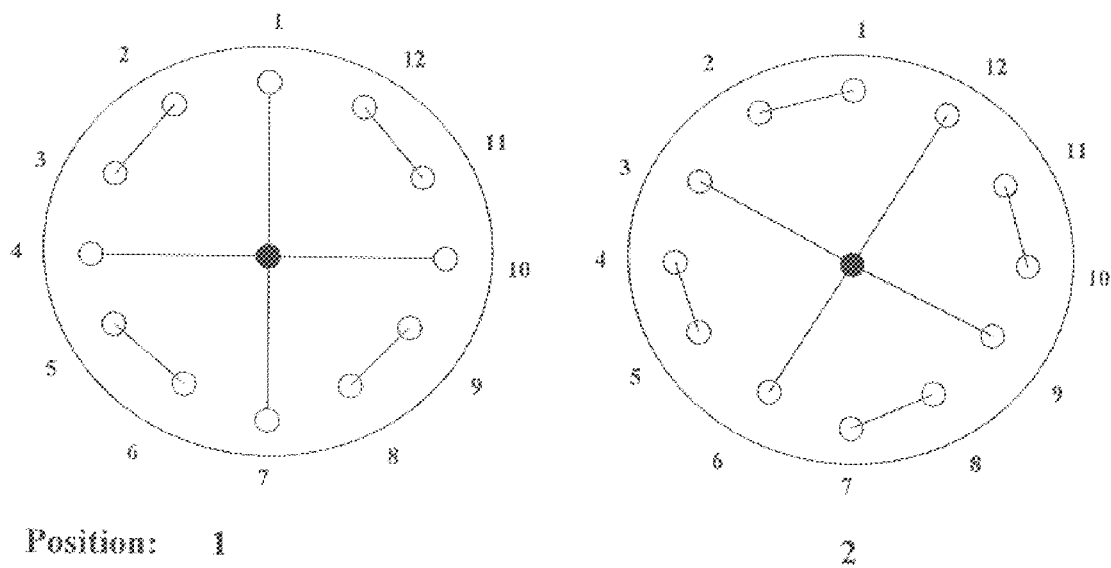
FIG. 3 depicts the configurations of the two valves of the injection system in loading mode (position 1) and injection mode (position 2).

In the case of simultaneous sample loading on several columns, one design for the sample injector of the present invention is shown in FIGS. 2 and 3. The interface between the injector and the multi-column unit is also illustrated in FIG. 2. Two head-to-head thirteen-port valves (valves A and B), connected with different sample loops and microtubes, make up the injection system for simultaneous loading of a sample solution onto a selected number of columns. Sample loop-1 ($S_1$) is installed between port-1 of valves A and B along with an electronically controlled shut-off valve right before the loop to prevent loading of the sample onto this loop if desired. Similarly, sample loops $S_2$, $S_3$ and $S_4$ are installed between ports 4, 7 and 10, respectively, of valves A and B with a shut-off valve upstream from each loop. Pump-1 ($P_1$), dedicated to the delivery of mobile phase 1 to column-1 ($C_1$), is connected to port-2 of valve A. Similarly, pump $P_2$ (dedicated to column $C_2$), pump $P_3$ (dedicated to column $C_3$) and pump $P_4$ (dedicated to column $C_4$) are connected to ports 5, 8 and 11 of valve A, respectively. All columns are connected to valve B: $C_1$ to port-2, $C_2$ to port-5, $C_3$ to port-8 and $C_4$ to port-11. Ports 3, 6, 9 and 12 of both valves A and B function as bridges between the pumps and their corresponding columns (loading configuration) or between sample syringe and the open end for waste (injection configuration). The central ports of valves A and B are connected to the sample syringe and the waste container, respectively. The arrows indicate the direction that the sample solution or solvent will flow. The sample loops in our invention can be of the same size or have different loading capacities.

The configurations of these two valves are shown in FIG. 3. In the loading configuration, both valve A and B are in position 1. The sample is introduced through the injection port (central port of valve A) and is loaded onto the different sample loops between ports 1, 4, 7 and 10 of valves A and B. At this point, the sample loops, initially filled with mobile phase, are loaded with the sample solution. If the sample loops are identical and no air bubble is accidentally introduced in the course of the injection, each loop should be loaded with an equal amount of the sample solution. Then both valve A and B are switched to the injection position (i.e., position 2) by a clockwise rotation of the valve rotor as shown in FIG. 3. At this point the sample loops find themselves connected to the corresponding pumps which deliver the mobile phases through the loops and push the sample onto the columns. This switching process can be done either manually or electronically. This 13-port valve sample injector design allows the sample loading process to be conducted without significant interruption of the mobile phase flow. The system may be configured so that the injection loops be connected in series rather than in parallel.

Pump System

As mentioned earlier, the particularity of the proposed invention is the use of dedicated pumps delivering the mobile phases to each column independently. A major limitation of using a single pumping system for all columns is that only similar columns (thus exhibiting similar back pressures) can be used to ensure perfect control of the mobile phase flow rates through the columns to optimize the quality of mass spectral analysis. This means that, in addition to limiting the system to a single type of columns per run, the same mobile phase composition and flow rate have to be used, which reduces the scope of application of the technique. For this reason, the implementation of a dedicated pump system is ideal, as it eliminates the concern of column back pressure control, which differs with columns and/or mobile phase compositions. The major advantage of having dedicated pumps is that the user can setup different flow rates or mobile phase compositions for each column, and can use different types and sizes (analytical or preparative) of columns run in parallel. This feature significantly expands the scope of applications of the present invention.

Eluent Switch System

The interface that Kassel and coworker used in the newly reported high throughput LC/MS with two columns and one mass spectrometer depends on the modification of the Ion-Spray interface to support flows from multiple columns. Shown in FIG. 4A, a parallel dual-sprayer interface was used for parallel preparative separations, and a sheath dual-spray was used for parallel analytical experiments (FIG. 4B). Each sprayer has its own nebulizer gas supply, which delivers 40 psi $N_2$ to enhance the nebulization and evaporation of solvents. The system can be fully automated to switch between parallel (dual) analytical and parallel (dual) preparative LC/MS analyses. Optimization of the signals from the two parallel sprayers was accomplished by Kassel and coworker by adjusting the spacing between the spray tips and the X-, Y-positioning of the dual-electrospray device relative to the entrance aperture (orifice) of the mass spectrometer.

The methodology can be adapted to our parallel multiple-column HPLC/MS system by making sheath (quadruple) electrospray with the nebulizer gas supply in the outer most position. One of the concerns for this design is how well the nebulizer gas will function and reproduce on this system when the positions of nebulizer gas with each column are different.

The problem of eluent switching between multiple columns and one detector can be solved by implementing the design described below, which can be implemented with existing commercially available technology.

FIG. 5 shows one example of the eluent switching system: after each column, a four-port solenoid valve is used to switch the eluent from the MS detector to fraction collector or waste according to a signal sent by a computer program interfaced with the whole system.

Figure 6:
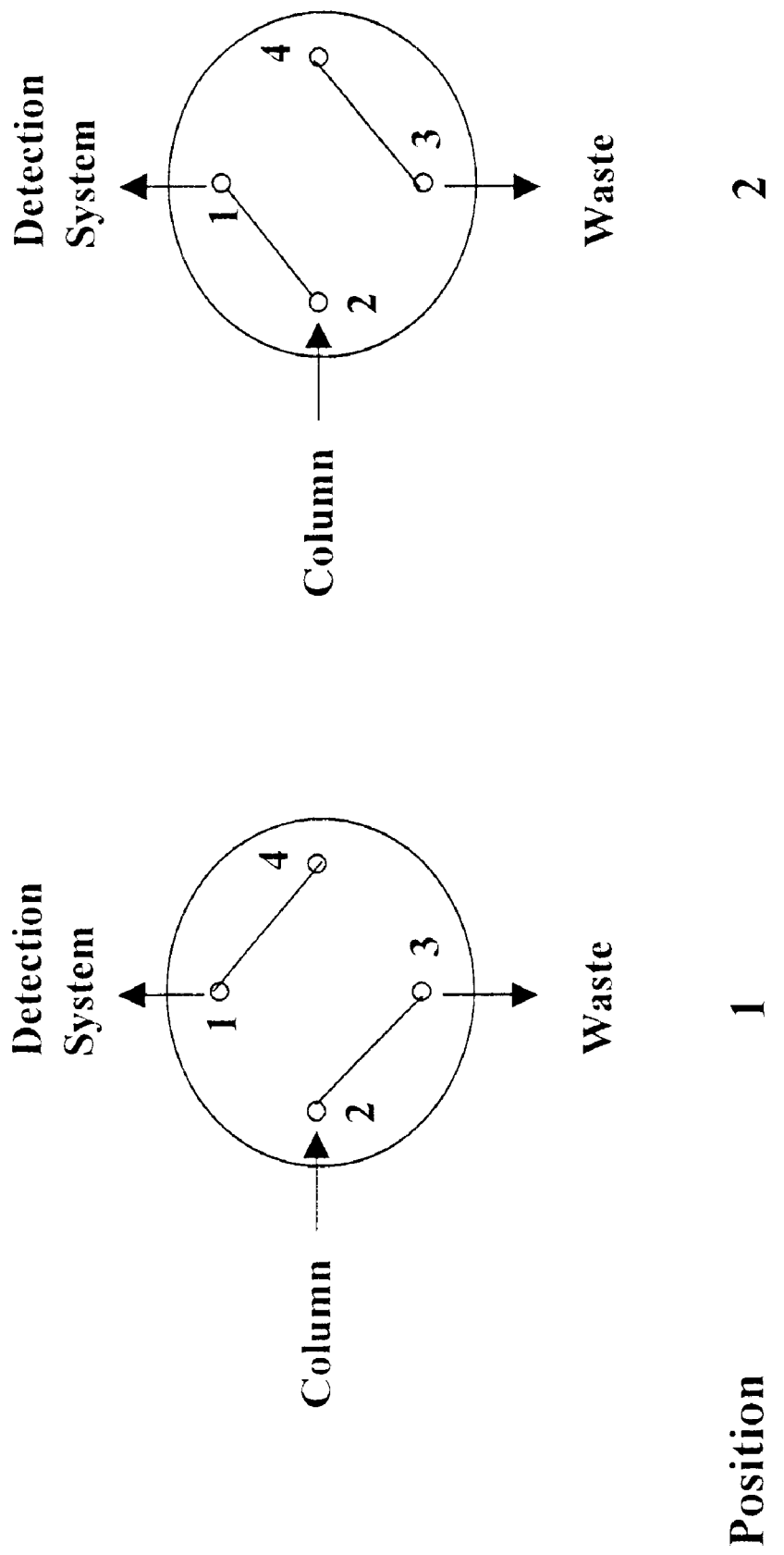
FIG. 6 depicts the hardware connections of the pre-detector four-port switching valve system.

The general advantage of solenoid valves is that the elution is continuous; consequently there is no disturbance on the flow rate, hence no disturbance regarding the capacity factor k'. Such valves are programmed for automatic operation, which can run for long hours to maximize the use of the mass spectrometer. The column-dedicated four-port valves used in this design are referred to as $V_1$, $V_2$, $V_3$ and $V_4$ for columns $C_1$, $C_2$, $C_3$ and $C_4$ respectively and their port connection and configurations are described in FIG. 6. The end of each column connected to port 2, and port 1 is connected to the electrospray ionization detector. Port 3 is connected to waste or fraction collection and port 4 remains unused. In position 1 the tunnels between ports 1 and 4 and between ports 2 and 3 are opened, so that the eluent from the column will go to waste or fraction collector. In position 2, port-1 and port-2 are connected, as well as ports 3 and 4, resulting in the eluent being delivered into the detection system. Electronic control (e.g., computer interface) of these valves allows their automatic opening and closing according to a programmed sequence resulting in the alternate sampling of each column in time blocks designated to the particular column.

The programming sequence is detailed in Table 1: each sequence cycle is divided into four quarters. The key feature of this programming is that the eluent from only one column is delivered into the detection system and the eluents from the other three columns are sent to the waste bottle (or fraction collectors) during each quarter. For instance, only $V_1$ is in position 2 (analysis) and the other three valves are in position 1 (waste) during the first quarter of the cycle. This means that only eluent from column $C_1$ can be detected during this period of time. Similarly, $V_2$, $V_3$ and $V_4$ are opened during the second, third and fourth quarter of the cycle, respectively.

TABLE 1

| Quarter | Valve | Position |
|---------|-------|----------|
| 1 | $V_1$ | 2 |
|   | $V_2$ | 1 |
|   | $V_3$ | 1 |
|   | $V_4$ | 1 |
| 2 | $V_1$ | 1 |
|   | $V_2$ | 2 |
|   | $V_3$ | 1 |
|   | $V_4$ | 1 |
| 3 | $V_1$ | 1 |
|   | $V_2$ | 1 |
|   | $V_3$ | 2 |
|   | $V_4$ | 1 |
| 4 | $V_1$ | 1 |
|   | $V_2$ | 1 |
|   | $V_3$ | 1 |
|   | $V_4$ | 2 |

After passing through the column, the eluent from each column enters a flow splitter, which divides the mobile phase into two streams, typically to both waste/fraction collector and a switch valve. The function of the splitter is to prevent back pressure changes to the column when the flow is restricted by the switch valve, i.e., when the switch valve is off the mobile phase needs a path to flow to avoid creating back pressure to the column. The flow splitters thus allow control of solvent volume that goes to the detector, waste, or fraction collector, but equally important is that they prevent any back pressure changes to the columns during the cycling of the switch valve. Preventing oscillating back pressure to the columns while the switch cycles should prevent column lifetime from changing compared to conventional single column chromatography.

After passing through the valve, the eluent from each column is transferred into a multiport manifold before entering the detection system (FIG. 5). This manifold enables the eluent from different columns to be delivered into the detection system through the same microtube. A washing cycle is incorporated to the system for each sampling, using solvent with a reference compound to minimize both the sample carryover and to set a reference for the chromatogram.

For one cycle of four-column sampling, the process for sampling, detection, and washing can take place simultaneously for all four columns, thus increasing the efficiency of mass spectrometer by four-fold. With some minor modifications to existing instrumentation and some unsophisticated hardware modifications to the HPLC system, a high-throughput LC/MS system is achieved.

Figure 7:
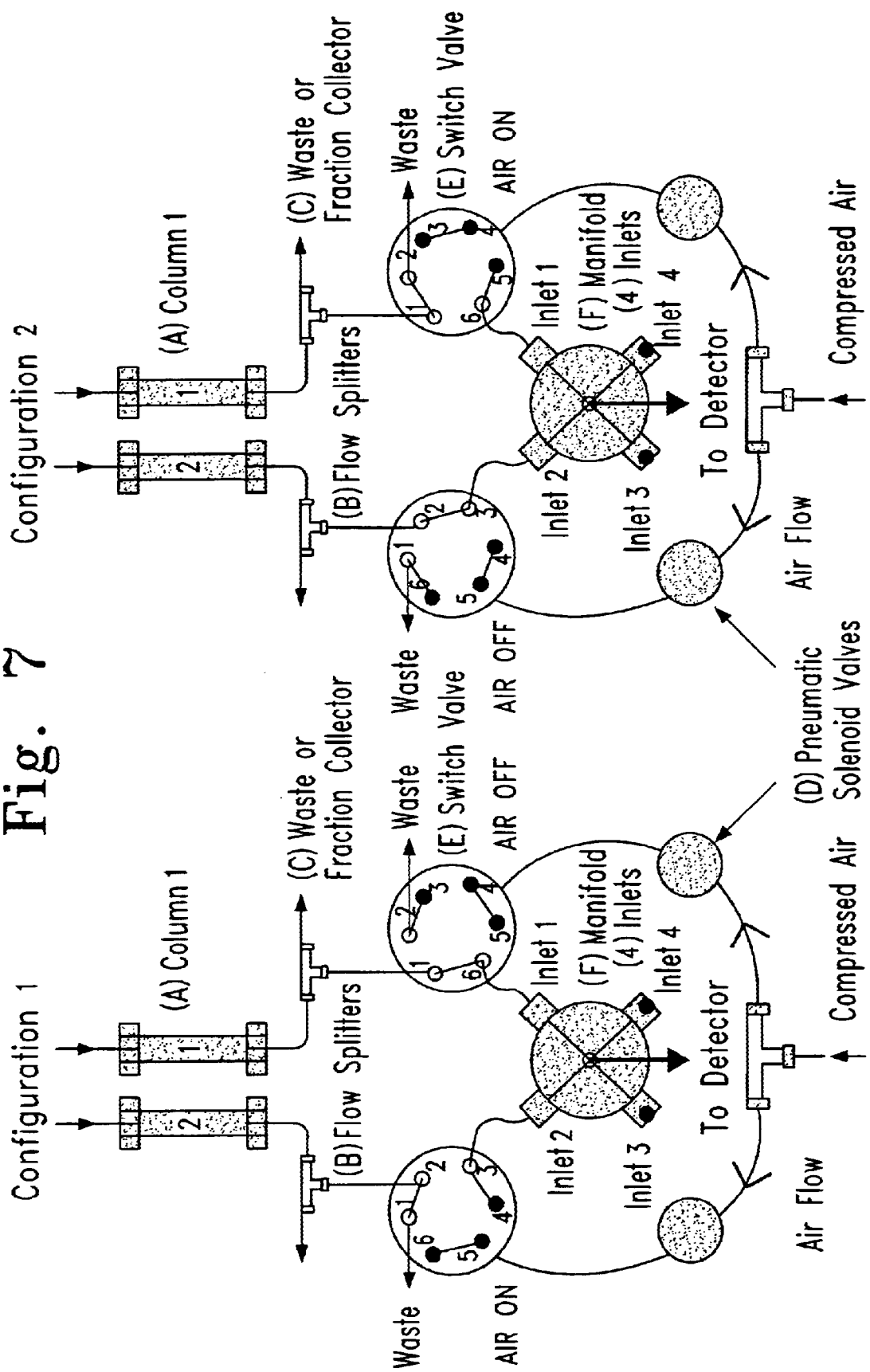
FIG. 7 depicts a schematic diagram of a prototype two-column eluent switch system. As shown, only two manifold inlets (1&2) are used for the two-column prototype. The remaining inlets (3&4) may accommodate two additional columns.

Referring to FIG. 7, which depicts a two-column eluent switch system, mobile phase eluting from column 1 (A) enters a flow splitter (B), which divides the mobile phase into two streams, typically to both waste (C) and a switch valve (E). The open/closed position of the switch valve is regulated by a pneumatic solenoid valve (D). Mobile phase is sent to the manifold and on to the detector when the switch valve is pneumatically opened; when the valve is closed the mobile phase goes to waste. Similar components are used for the second column.

Although a 4-port diaphragm valve would be sufficient to build the device, we were unable to find a commercial source for it. Valco is the only commercial supplier of diaphragm valves, and they only manufacture 4-port valves with incorporated internal sample loops (0.5 and 1 $\mu$l), which cannot be used for our purposes. We thus opted for the next available model: a 6-port valve, which can easily be configured to function as a two-position 4-port switch valve and has the added flexibility of using the three extra ports for additional features if desired. The 6-port switch valve (Valco DV22-2116) utilizes a low dead volume (~2 $\mu$L) flexible diaphragm to open and close ports with short actuation times ($\leq 10$ ms). The actuation frequency was regulated by an electronic controller which was interfaced with the system by James Hill Instrument Services (28 Henderson Street, Arlington, Mass. 02474) and was set at ~1 Hz. Pneumatically controlled diaphragm valves have lifetimes of $>10^6$ cycles, whereas rotor type valves have lifetimes of ~$10^4$ cycles. The limited life-times of rotor valves limit their use in designing parallel chromatography equipment that will cycle >86,000 times (at 1 Hz) over a 24 hour period. In addition to extended lifetimes, the rebuilding cost for the diaphragm valves is significantly less. Only the diaphragm itself needs to be replaced at very low cost. Diaphragm replacement should be infrequent; continuous operation for 2 weeks was achieved without any detectable loss of valve function. Note that since each column-valve unit is separately connected to the manifold, adding or removing columns from the device is simple, i.e., this flexible-manufacturing feature of the design allows the user to configure any number of columns.

Summary of Preliminary Experimental Results
Using The Two-Column Eluent Switch System
Shown in FIG. 7

I. Phosphate Buffer Solution

The Phosphate Buffer Saline (PBS) solution was prepared by dissolving 0.2 g of potassium phosphate monobasic, 1.15 g of sodium phosphate dibasic and 2.922 g of sodium chloride in 1 L of distilled water. This produced a PBS buffer with a 0.01M phosphate, 0.067M salt and pH around 7.5.

II. LC/MS Conditions

The LC/MS system comprised a Hewlett Packard HPLC (HP 1100 series) interfaced with an Esquire__MS spectrometer. The HPLC had two binary pumps and a Diode Array detector (DAD). The mobile phase was a 0.01M PBS solution with 15% Acetonitrile and the flow rate was set up to 1 ml/min unless otherwise indicated.

III. Testing the Eluent Switch Without Columns

Preliminary studies were performed to test the operation of the switch valves in different solvents. This was necessary because this is the first time this type of valve, which has been designed for use with gas chromatography, had been used for liquids (Valco, personal communication). These preliminary studies were intended to show that the valve could function for weeks in typical mobile phases (buffers with and without organic modifiers). Acetonitrile, water, and 0.01M phosphate buffered saline were perfused through the system. These mobile phase conditions, salt, etc., did not clog the manifold or ruin the diaphragm.

We operated the eluent switch at 1 Hz for ~11 days of 24 hour operation (~$10^6$ cycles) without loss of valve performance. These preliminary solvent stability studies were sufficient for us to connect columns to the system.

IV. Testing the Eluent Switch With Columns

Unless otherwise indicated, the experimental data reported in this section was collected under the following conditions: UV detection at 280 nm, UV flow cell: 14 $\mu$L, mobile phase: 15% acetonitrile in PBS buffer at 1 mL/min., injection volume: 10 $\mu$L (sample amount: 2 $\mu$g), eluent switch rate: 1 Hz/column, and one pump per column (one binary pump used at two different pumps).

The primary purpose of these studies was to verify that there was little if any change in peak position, $t_r$, and peak width $\omega_{0.5}$ and also to verify that column stability was not significantly affected by the switch. Retention time data is reported as capacity factors $k'=(t_r-t_o)/t_o$. The most critical preliminary data to obtain, however, was to experimentally determine the minimum peak washing times (volumes) needed to obtain good chromatographic peak characterization with the hardware designed and assembled as shown in FIG. 7.

Figure 8:
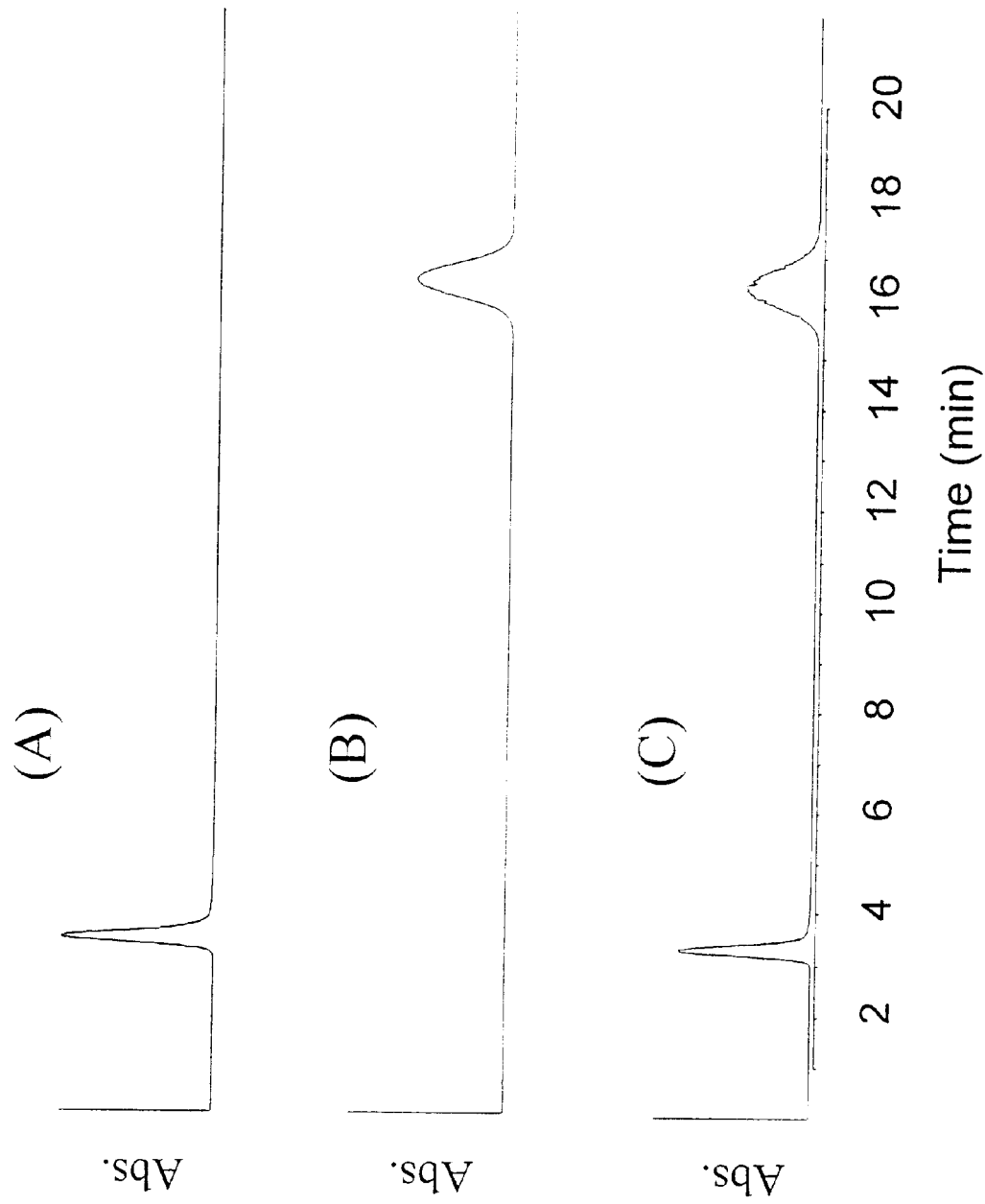
FIG. 8 details elution of 4-methylanisole from an $^{Ester}$IAM.PC$^{C10/C3}$ column, a C8 column, and from both columns in parallel.

Note that our preliminary design (FIG. 7) does not allow any control of the data acquisition or storage from conunercial detectors. In other words, data from two columns is stored into one data file, and therefore one chromatogram is generated when two columns are connected to the eluent switch. Nevertheless, an unambiguous experiment was designed using 4-methylanisole as a test solute to test whether $t_r$ and $\sigma$ change when the eluent switch controls mobile phase flow to the detectors. The compound 4-methylanisole has $t_r$ values on $^{Ester}$IAM.PC$^{C10/C3}$ and C8 columns of ~3.5 min and ~16.5 min respectively; hence, which column this test solute elutes from can be determined by $t_r$ values. As shown in FIG. 8 (chromatograms) and Table 2, small percent changes in $t_r$ and s occurred when 4-methylanisole elutes with and without the eluent switch.

switching is sufficient to eliminate mixing between the mobile phases, oscillation is expected because the mobile phase from the IAM column is effectively a wash cycle that should drive the signal to baseline.

Note that the peaks in FIG. 8C do not show oscillations as the peaks elute (i.e. signal returns to baseline). This indicates that there is significant mixing in either (i) the manifold (~1–2 $\mu$L dead volume), (ii) post manifold tubing (1–2 ~L dead volume), (iii) the UV detector cell (~14 $\mu$L dead volume), (iv) an unknown source, or some combination of (i), (ii), (iii), and (iv). An important concept is that when the flow rate is 1 mL/min, ~17 $\mu$L/sec flows through the system. At 1 Hz (sec) per channel, 17 $\mu$L of mobile phase elutes though the system and this volume of mobile phase should have been sufficient to wash components (i), (ii), and (iii). It is essential that these common post column conduits, shared by both column eluents, are washed. In other words, to validate the prototype design (FIG. 7) it was essential to demonstrate that sufficient extra column washing could be done to obtain good peaks, peak shapes, etc.

Elution of 4-methylanisole from $^{Ester}$IAM.PC$^{C10/C3}$ and C8 columns was performed using the eluent switch shown in FIG. 7 (eluent switch rate: 4 sec/column) and one pump to control the flow to both columns. Using one pump to perfuse both columns results in 1.3–1.4 mL/min perfusing the IAM column and 0.6–0.7 mL/min perfusing the C8 column (See FIG. 9). Several important observations should be noted about FIG. 9.

1. The C8 and IAM columns have different packing materials, and therefore different resistance to mobile phase flow for a given flow rate. Consequently, using one pump per column (FIG. 8) accurately controlled flow rate (1 ml/min) through both columns. Thus, as expected, using a single pump for two columns divides the mobile phase according to the back pressure differences in the two columns. When one pump was used (FIG. 9), a 2 mL/min flow rate resulted in 1.3–1.4 mL/min perfusing the IAM column, and 0.6–0.7 mL/min perfusing the C8 column. Thus the $t_r$ of 4-methylanisole decreased on the IAM column, and increased on the C8 column.

TABLE 2

$^{Ester}$IAM.PC$^{C10/C3}$ and C8 chromatographic data for 4-methylanisole. Chromatograms are shown in FIG. 8

| | Columns | | | | | |
|---|---|---|---|---|---|---|
| | $^{Ester}$IAM.PC$^{C10/C3}$ | | | C8 | | |
| | $t_r$ (retention, min) | k' (Capacity factor) | $\omega_{0.5}$ (peak width) | $t_r$ (retention, min.) | k' (Capacity factor) | $\omega_{0.5}$ (Peak width) |
| No Switch (Single column chromatography) | 3.31 | 7.48 | 0.46 | 15.85 | 23.04 | 1.57 |
| Eluent Switch (parallel chromatography) | 3.17 | 7.13 | 0.44 | 16.3 | 23.71 | 1.35 |
| Percent Change | 5.1 | 4.7 | 4.3 | 2.8 | 2.9 | 14 |

Figure 9:
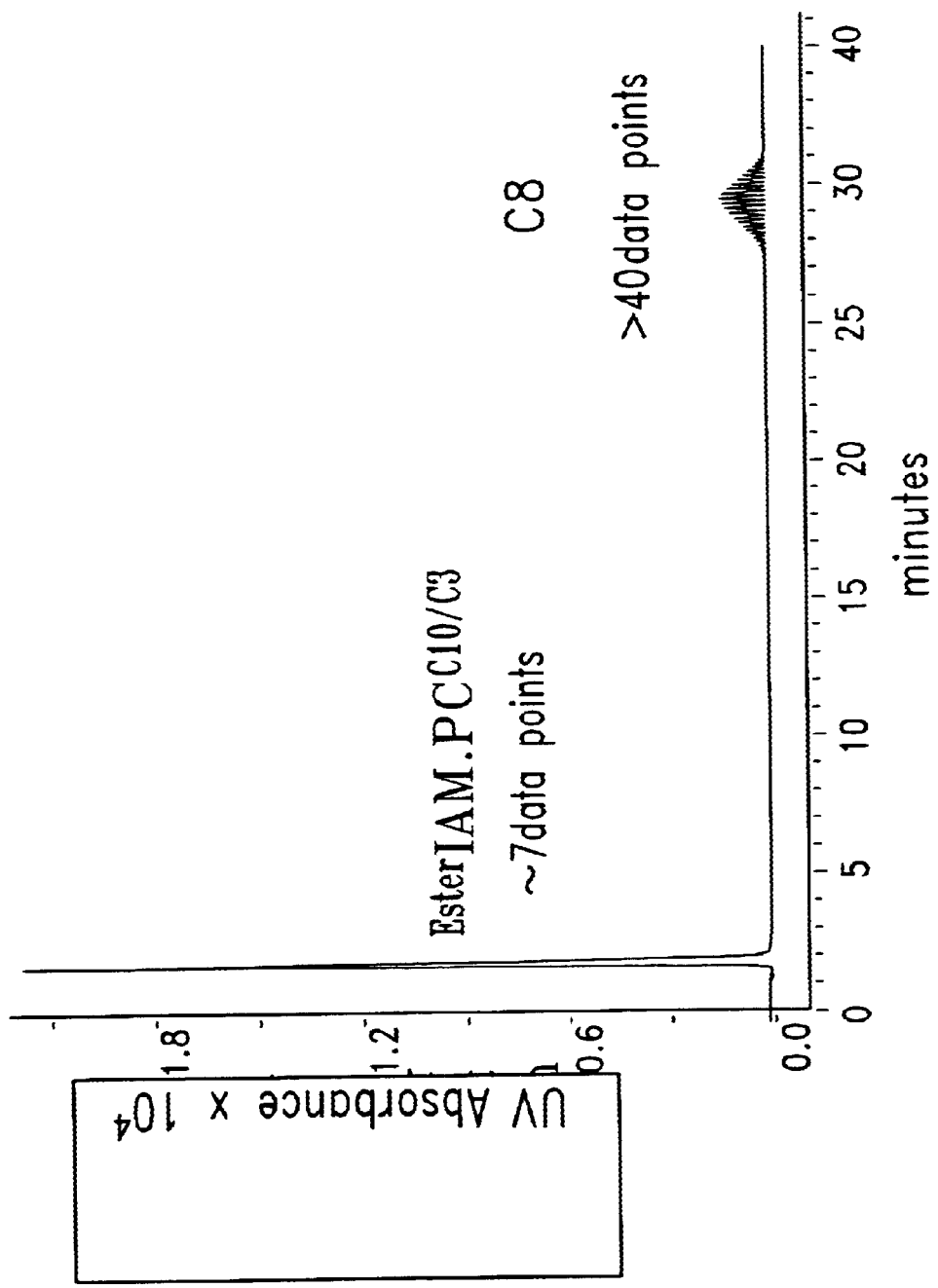
FIG. 9 details elution of 4-methylanisole from $^{Ester}$IAM.PC$^{C10/C3}$ and C8 columns using the eluent switch of FIG. 7 and one pump for both columns.

When 4-methylanisole eluted ($t_r$~16.5 min) from the C8 column (FIG. 8B), mobile phase from the IAM column (FIG. 8A) does not contain 4-methylanisole. Thus at 1 Hz eluent switching, the expected chromatograms should contain intervals of no absorbance from the IAM mobile phase (~1 sec), followed by absorbance from 4-methylanisole (~1 sec) from the C8 column. In other words, when eluent 2. The data points per peak are controlled by both the elution time and eluent switch rate. A 4 sec/column (0.25 Hz) eluent switch rate resulted in only 7 data points to characterize the peak eluting at $t_r$~2 min, whereas >40 data points were obtained for the peak at ~29 min (FIG. 9).

The inexpensive custom controller (not shown in FIG. 7) can only regulate equal open/closed times; different flow rates on each column were not possible for the instrument used to obtain the preliminary data. Nevertheless, this device was used to experimentally determine the volume of washing needed to obtain the appropriate chromatography peaks with oscillations that approach the baseline. Thus, as shown in FIG. 9, 4 sec/column (~60 $\mu$L/sec) generated an excellent chromatogram for 4-methylanisole eluting from the C8 column. However, in the case of the IAM column, where the retention time was short (~2 minutes), undersampling of the peak data occurred.

Figure 10:
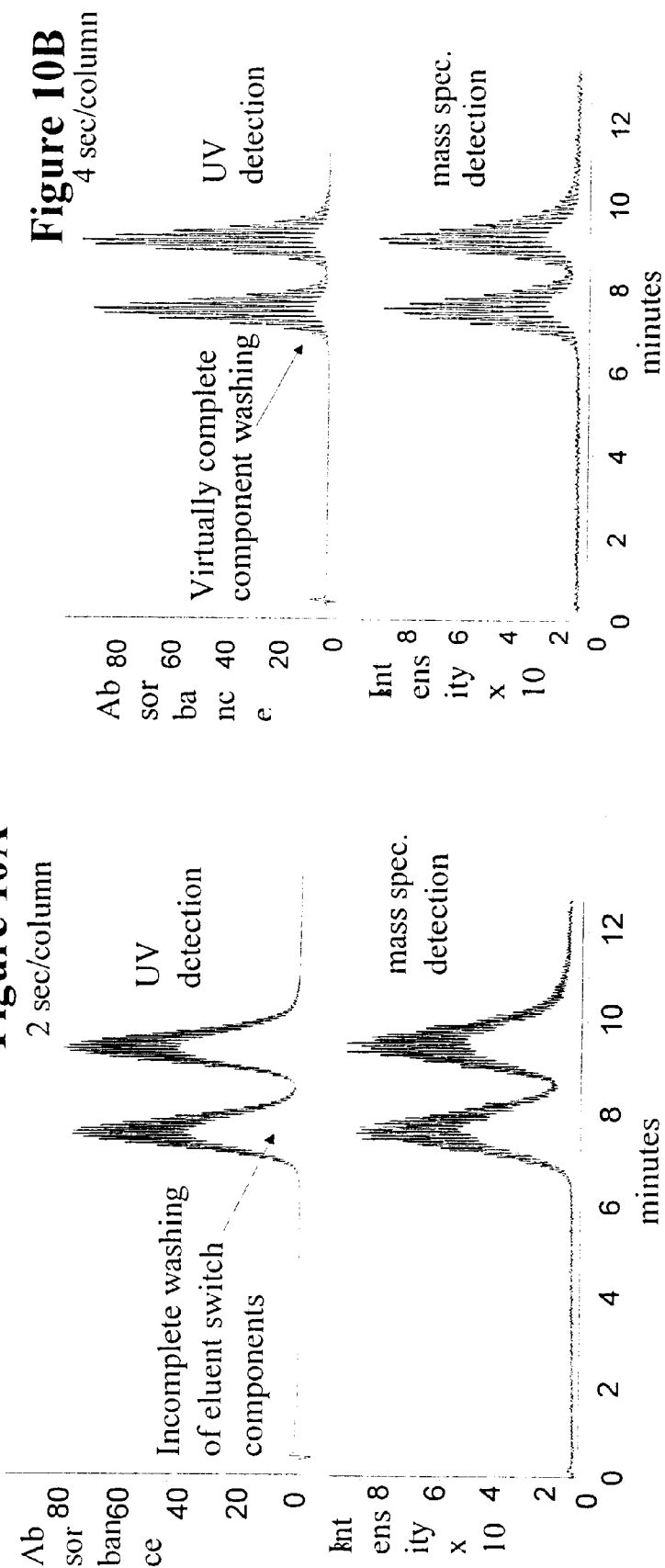
FIG. 10 details data obtained using the eluent switch of FIG. 7 in a one-pump/two-column set up.

Liquid chromatography equipment interfaced with mass spectrometers is typically utilized with a UV detector. Consequently, we evaluated the eluent switch on a Bruker Esquire mass spectrometer equipped with a photodiode array detector (PDA). For these studies Estazolam (high ionization efficiency) was substituted for 4-methylanisole (low ionization efficiency). FIG. 10 compares 2 sec/column (FIG. 10A) and 4 sec/column (FIG. 10B) eluent switch rates for Estazolam eluting from an $^{Ester}$IAM.PC$^{C10/C3}$ and $^{Ester}$IAM.PS$^{C10/C3}$ columns (synthesized in-house at CPBD) using a single pump to deliver the mobile phase at 2 mL/min., which equally splits between the two columns of identical size, particle size, shape and porosity. For this experiment 4 sec/column at 1 mL/min was not quite enough to bring the oscillations to baseline; a slightly higher rate would be needed. Nevertheless, FIG. 10 demonstrates that excellent peak characterization occurs when the system is washed.

V. Analyte Calibration Curves Can be Obtained From Two Columns and Column Stability Does Not Change Calibration curves are essential for parallel chromatography to be used for quantitative analysis. Calibration curves and column stability data were generated for 4-methylanisole on $^{Ester}$IAM.PC$^{C10/C3}$ and C8 columns using UV detection with an HP1100 HPLC system and the manifold switch shown in FIG. 7. It was shown that calibration curves are not affected by the eluent switch. In addition, column life times changed little to none when columns were modulated with the eluent switch. After ~8000 column volumes, less than 5% change in k' occurred on the IAM column whereas there was little change on the C8 column.

Other embodiments of this design are identical to the hardware shown in FIG. 7 with the modification that 2 additional units can be added. Another modification is that an extra switch valve can can be plumbed to a 6-port manifold for washing purposes. Thus, four of the six manifold ports can be plumbed to 4 different columns. Of the two remaining manifold ports, one can be used to send eluent to the detector and the other manifold port can be used to introduce a wash cycle between columns.

In another embodiment of this design the flow splitter (FIG. 7) is a pressure release valve, which functions as a flow controller. Such modification is to accommodate detectors for which the LC eluent flow rate is limited. For example, the MS system cannot tolerate high chromatographic flow because of both pumping capacity and detector sensitivity limit. The advertised maximum LC flow rate tolerated by the Esquire-LC (the model of LC/MS instrument used for the validation studies supporting this patent) is 1.0 ml/min. Based on this consideration, when high LC flows (>1.0 ml/min) are required for a particular study, the LC effluent needs to be split prior to entering the MS detector so that the LC flow entering the detector does not exceed 1 mL/min. A flow controller (or pressure release valve) such as the model manufactured by Upchurch Scientific, Oak Harbor, Wash., may be used to split the eluent flow, keeping the flow to the MS detector within the range tolerated by the instrument.

In another embodiment of the present invention, additional optional components such as in-line pH-meters and pressure sensors may be incorporated in the design. In-line pH monitoring finds use in pH dependent experiments, such as those aimed at determining parameters such as $^{bulk}$pKa and $^{surface}$pKa. Pressure sensors may be used to evaluate column performance, or for experiments requiring variable mobile phase flow rates.

A wash cycle is important for removing both solute and solvent carryover between columns (FIG. 10). Washing the manifold (~2 $\mu$L dead volume) post manifold tubing (~4 $\mu$L dead volume) and UV detector cell volume can be done with different volumes of solvent depending on the exact configuration of the system. The wash cycle can prevent mixing of non-compatible solvents, precipitation, channeling, and sample mixing between. Note that 8- or 16-port manifolds can be purchased and more than one wash cycle can be designed if needed. Experimental testing of different mobile phases provides the experimental data needed to determine if more than one wash cycle is needed to provide a versatile robust commercial instrument.

In one embodiment of the invention, the manifold is directly connected to, or incorporated within, the "detector cell." For the purpose of the invention, "detector cell" designates the component of the detector where the incoming eluent from the LC is analyzed. Examples of such "detector cells" are electrospray needles (MS) and flow cells (UV). Thus, the manifold is reduced to a low dead volume adapter that may be assembled directly onto the detector cell, provided minor modification of said detector cell. This would allow significant reduction of the dead volume created by the tubing connecting the manifold and the detector, thus minimizing band broadening effects. In addition, this would reduce the wash cycle time, and therefore would enhance resolution in data acquisition. Alternatively, the "detector cell" may be designed and/or manufactured so that it has multiple inlets to accommodate for multiple incoming LC eluent lines (for example four lines for each column eluent, and one for the wash solvent).

A 6-port manifold system requires a new controller device to be constructed. Such controller should operate the switch valves for each of the four columns and the timing of the wash cycle. A preferred controller will allow 1, 2, 3, or 4 columns to be used at any time. This goal can be acquired by having full computer control of the eluent switch valves. Valve switching can be actuated by TTL signals from an A/D board in a dedicated PC computer system. A software interface to the A/D board can be programmed using the LabVIEW computer programming language or other useful computer language. Such custom-made program can control the timing of the flow of each of the four columns and the wash cycle. In order to optimize performance of the system, the timing of each of the column cycles, as well as the wash cycle, can be controllable programmatically and can vary. Thus, column flow to the detector from different columns can be 0.5 sec for the first column 0.7 sec for the second, and any other value for the other columns. The wash cycle between columns is also variable.

Data Indexing Methods

Data from multiple columns can be stored into one data file only if unambiguous indexing of the signal from each column can be incorporated into the data file. An indexing method is needed to accomplish identification of each column's data in one data file.

For this purpose, a method for data acquisition by analysis of eluent streams from multiple chromatographic columns using an eluent stream analyzer that has a fluid sampling port and is capable of providing signals characteristic of detected chemical species is useful. An embodiment of this method comprises providing an eluent switching valve having (1) fluid input ports in fluid communication with the eluent stream from each chromatographic column and with a source of at least one indexing fluid, (2) a fluid output port in fluid flow communication with a fluid sampling port on the eluent stream analyzer, and (3) a valve system communicating with a programmable controller for directing aliquots of the respective eluent streams and indexing fluid in a programmed sequence through the fluid output port and toward the fluid sampling port on the eluent stream analyzer, and correlating the electronic storage of signals from the analyzer with the programmed sequence so that analyzer signals from analysis of the aliquots of eluent of each respective column are stored in an algorithm accessible electronic storage device, such as a computer. In further embodiments of this method, the correlation of the electronic storage of signals from the analyzer include the step of sensing aliquots of indexing fluid between each eluent stream aliquot. Such indexing fluid is generally a liquid with some characteristic detectable by the analyzer, but in various embodiments, the indexing fluid may be in the form of a gas or a gas/liquid combination.

In this method, the chromatographic system can further comprise a pump for controlling pressure or a valve for controlling rate of flow of the respective eluent streams and indexing fluids through the valve system and toward the fluid sampling port on the eluent stream analyzer. Further, this method can be used wherein the respective aliquots of indexing fluids between aliquots of the respective eluent streams are of programmable unique volumes. Optionally, the controller for the valve system is programmed to deliver at last one aliquot of indexing fluid through the output port between each eluent stream aliquot. Other options include methods wherein the analyzer senses the respective indexing fluid aliquots and directs the signals from the next following eluent stream aliquot to a predetermined electronic data storage register where eluent aliquot analysis signals for each respective chromatographic column is stored in an accessible format. Further components of chromatographic system that are potentially useful are items such as a flow rate detector and a flow rate controller for each chromatographic column.

Other embodiments of such data acquisition/indexing systems are provided herein. An example of such embodiment involves the use of: (1) a multi-column chromatographic system comprising at least two chromatographic columns having a mobile phase input port and an eluent stream output port; (2) a mobile phase delivery system in fluid flow communication with the mobile phase input port, and (3) an eluent stream analyzer having a fluid sampling port and capable of providing signals characteristic of chemical species in a fluid received in said sampling port. To these components is attached an eluent switching valve assembly having (1) a fluid input port positioned for fluid communication with the eluent stream from each chromatographic column and with a source of at least one indexing fluid; (2) a fluid output port in fluid flow communication with the fluid sampling port of the eluent stream analyzer; and (3) a valve system for directing aliquot volumes of the respective eluent streams and indexing fluid in a programmed sequence through the fluid output port and toward the fluid sampling port on the eluent stream analyzer.

Typically, an electronic data storage device is used for receiving and storing signals from the eluent stream analyzer representative of analysis of eluent stream aliquots of each respective chromatographic column, and also included is a programmable controller (computer) including an algorithm including instructions for sensing the presence, volume or components of an indexing fluid aliquot at the fluid sampling port of the analyzer and directing signals from the analyzer for eluent stream aliquots corresponding to the respective chromatographic columns to electronic data storage registers/devices designated for data storage for the respective chromatographic columns.

In general, the multi-column chromatographic system for data indexing described above uses a fluid input port on the eluent switching valve assembly that is positioned for fluid communication with the eluent stream from each chromatographic column and with a pressure control source of at least one indexing liquid and at least one indexing gas. Analyzers useful for this method include, but are not limited to, mass spectrometers, infra-red spectrometers, nuclear magnetic resonance spectrometers, and ultraviolet spectrometers, fluorescence detectors, electrochemical detectors, and refractive index detectors.

One method to accomplish such identification involves using a wash cycle to index chromatography files for the high throughput HPLC instrument. For instance, a long wash pulse (no signal) at the beginning of the chromatographic experiment (i.e., before solute injection on any column in the high throughput HPLC instrument), can be used to flag the onset of an injection in the data-file. Also, slightly different volumes of wash between eluent switching of different columns will result in slightly different 'blank-signals' in the data file. The size of the 'blank-signals' throughout the single data-file can then be used to decode the unique detector data-file into multiple chromatograms.

Knowing which chromatogram the current data is associated with is a matter of knowing the valve positions at any given time. For example, if the current valve position is allowing flow from column 1 then the data will be added to the window associated with chromatogram 1. Wash cycle data will likely not be saved, but of course the option to save this data exists. Note that in order for this scheme to be successful, data should only be included in a given chromatogram after enough flow has passed through the detector cell to completely wash out the previous stream.

The signal received by the analyzer may be used as "feed back" signal to control the eluent switch valves. For instance, if the wash solvent contains a reference compound and the analyzer is a mass spectrometer, when the MS detects the signal corresponding to the reference compound (indicating that the wash solvent is being analyzed), a signal is sent to the eluent switch controller to change the valve configuration, so that eluent from the next column that is to be analyzed is directed to the detector, and the wash solvent is directed to waste.

Figure 11A:
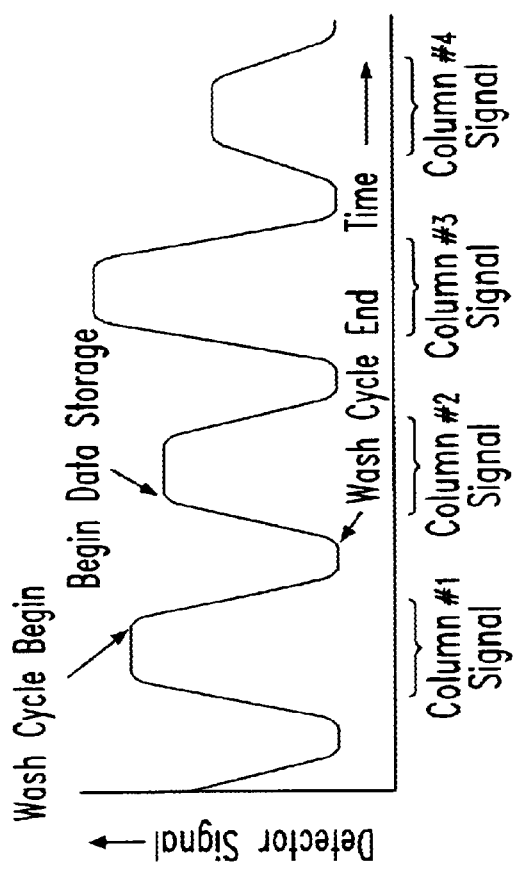
FIG. 11 is a schematic demonstrating one embodiment of data indexing useful in the present invention, and experimental data showing the UV detector signal profile for the elution of Warfarin on $^{ester}$IAM.PS$^{C10/C3}$ using the eluent switch system shown in FIG. 5.

FIG. 11 is a schematic of the type of time-dependent absorbance data seen using the present system. At the beginning of the wash cycle there is a rapid change in signal as the detector-cell is purged. The signal then reaches a steady state (plateau, FIG. 11A) indicating that washing is complete. This phenomenon can be used to determine an optimal wash cycle duration. As the eluent flow to the detector is switched to a column, there is another rapid change in the signal followed by a steady state. The signal from that steady state time slice will be added to the chromatogram for that column.

Figure 11B:
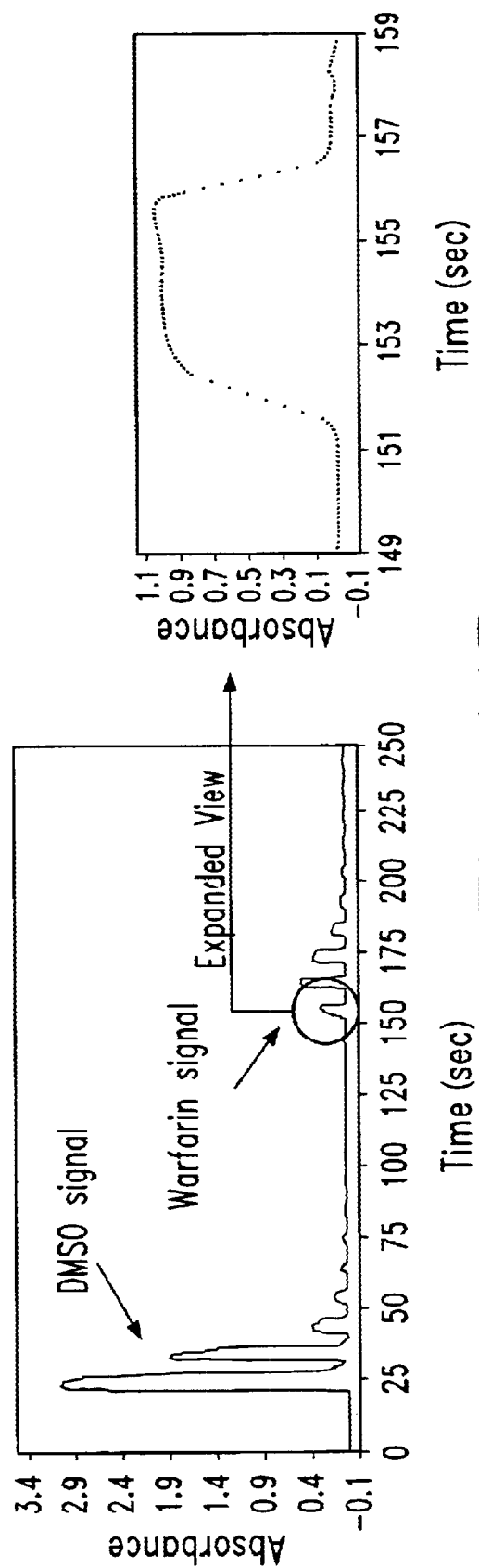

An alternative to using a fixed duration wash cycle would be to end the wash cycle or begin data acquisition only when the detector signal has reached a steady state (FIG. 11A). This option would allow for wash cycles to be as short as possible while ensuring that a complete wash has been completed for all column outflows. Such a scheme is especially desirable when the eluent composition from each column (and therefore the washing rates) are significantly different. The data in FIG. 11A is somewhat idealized in that it shows no change in the signal while data is being stored to a chromatogram. If this data is collected during the elution of a peak it may actually undergo a significant change. The software used in the present system must be able to distinguish between a rate of change characteristic of washing and that due to changing analyte concentration. This is possible since the rate of change from washing should be much higher. FIG. 11B shows data collected on a High-Throughput HPLC/UV ($^{HT}$HPLC-UV) instrument (the design of which is shown on FIG. 5, where the detector is a UV-Vis detector) using one of the available four channels (columns). The graph shows the elution profile (UV detection) for a sample of Warfarin (0.6 μg/μL in DMSO/PBS 30/70; injection volume: 20 μL) on an $^{ester}$IAM.PS$^{C10/}$$c_3$ column (4.6×30 mm; 15% acetonitrile in PBS, 1 mL/min). The eluent switch rate was set at 5 seconds per switch. The expanded view (FIG. 11B, right) of the signal around 150 sec is in agreement with the theoretical absorbance data profile shown in FIG. 11A.

We initially focused on experiments that generated non-overlapping peaks (FIGS. 8–10). Other tests were performed to verify that different wash cycles can be used to index and deconvolute chromatographic data files containing data from multiple columns. The hardware design used allows for each column and wash cycle to be cycled in any variety of order.

Figure 12:
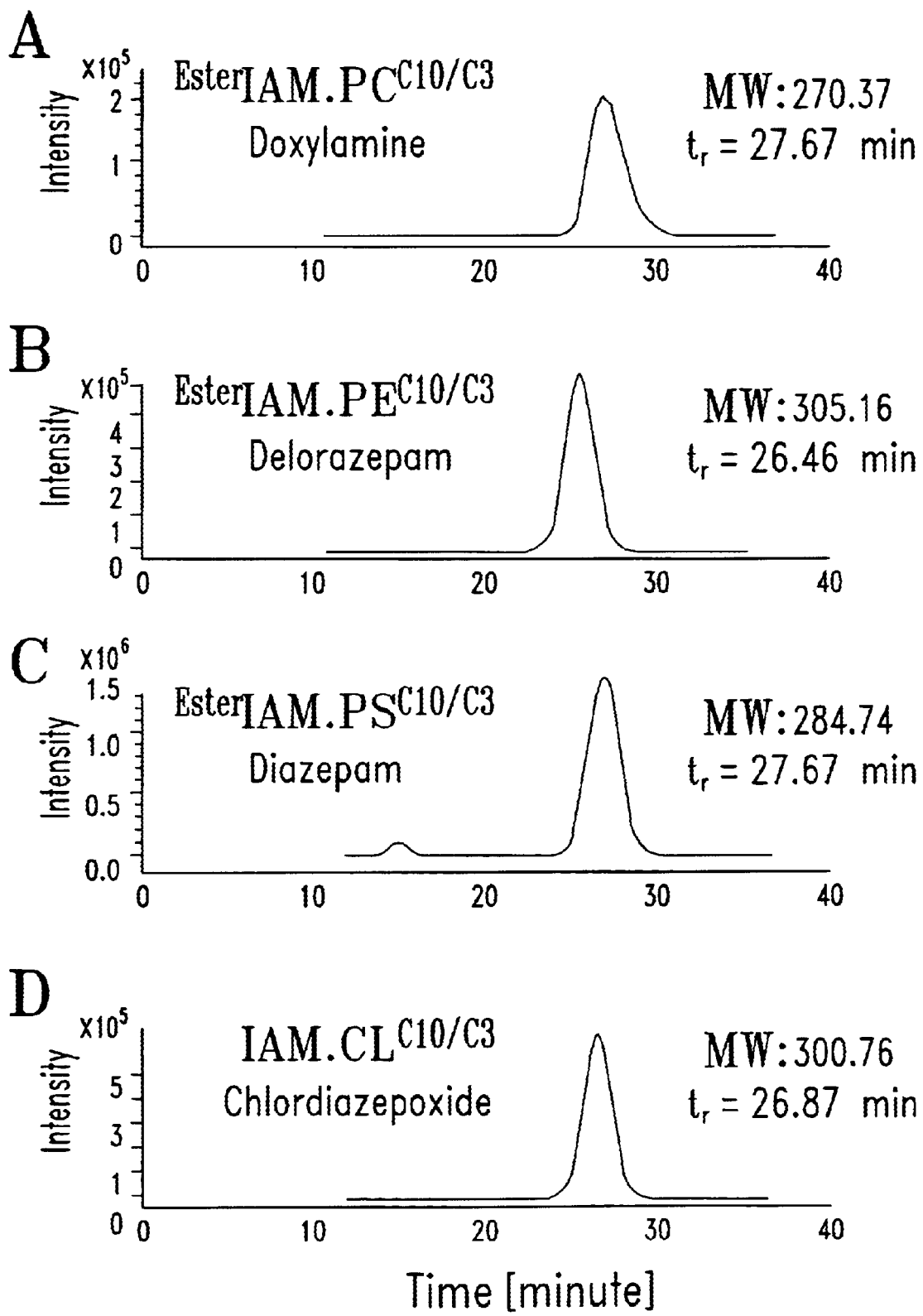
FIG. 12 details the chromatograms of four drugs with similar membrane binding properties from single column chromatography.
Figure 13:
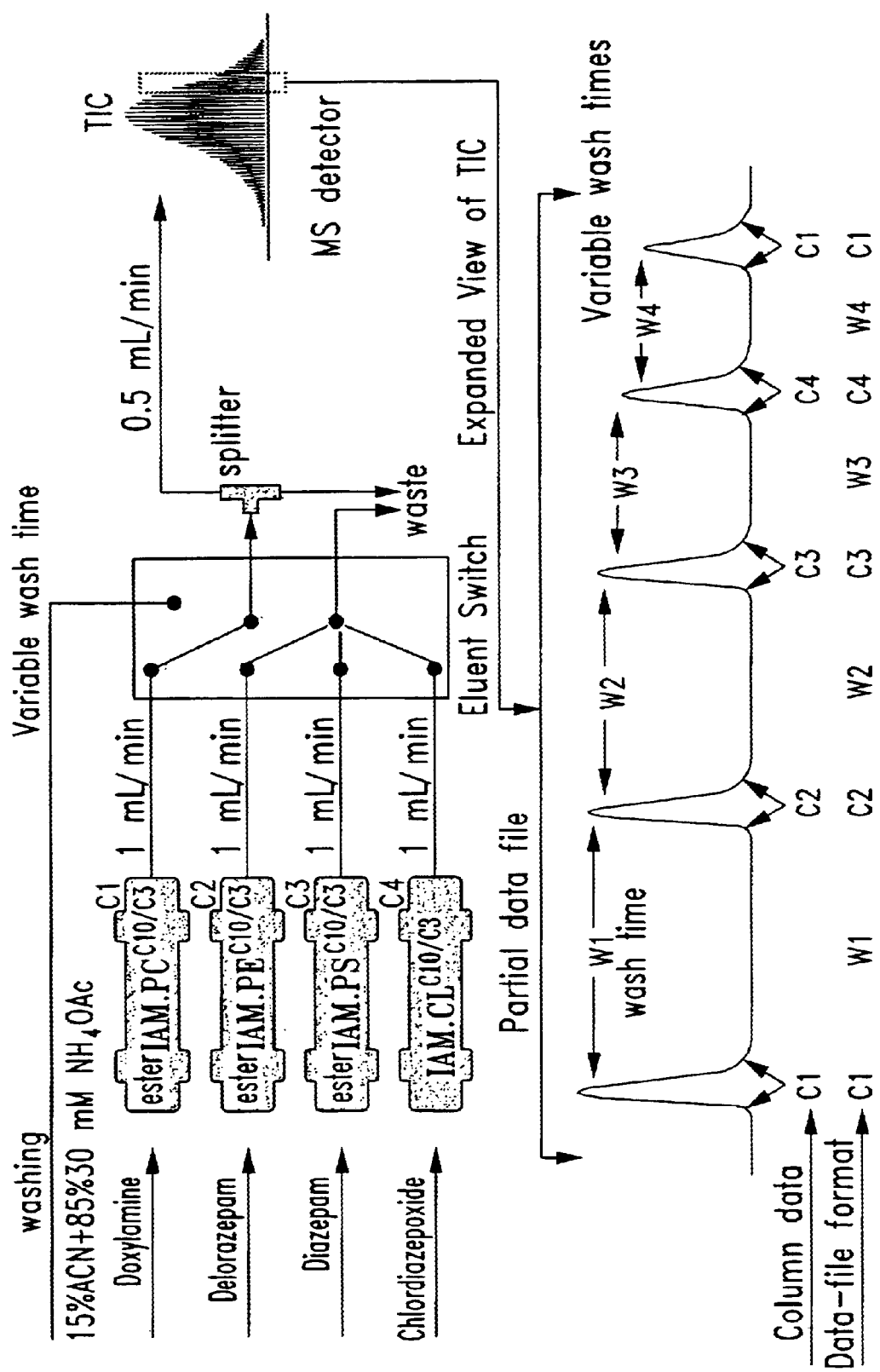
FIG. 13 is a schematic demonstrating exemplary data using the eluent switch method and parallel chromatography, as well as data indexing useful in the present invention.

FIG. 12 shows the single elution of 4 different drugs from 4 different IAM surfaces using a mass spectrometer as a detector and single column chromatography. Note that these compounds have similar retention times and that parallel chromatography that utilizes one detector will unavoidably have all of the compounds co-elute to variable degrees through the common detector. Molecular weight differences provide the needed information to generate chromatograms. Thus, these compounds can be used as solutes for testing the present invention. The experimental design is shown in FIG. 13.

Parallel chromatography generates overlapping peaks in the total ion chromatogram (TIC). One data-file will exist as opposed to the 4 data-files generated by single column chromatography (FIG. 13). Individual chromatograms for each column can be extracted from the single data file. Variable wash cycles set the file format of the data-file as depicted in FIG. 13. For instance, in the partial data-file above, chromatographic data from column 2 follows a long wash pulse (W1), whereas the chromatographic data from column 3 follows a shorter wash (W2). Thus when W1>W2>W3>W4, the chromatographic data C1, C2, C3, and C4, corresponding to column 1, column 2, etc, can be extracted from the data-file. Effectively, variable intercolumn wash cycles allow us to experimentally control file formatting during parallel chromatography, which may be accessed after the chromatography experiment in real data acquisition time.

Robust analytical methods like mass spectroscopy are particularly useful because they allow for selective ion monitoring of compounds that co-elute during chromatographic experiments. Thus, it is routine for mass spectrometers to elucidate compounds co-eluting from columns and this is particularly important for scientists evaluating chemical libraries. Being able to store chromatographic data into one detector-data-file without modifying (1) the detector itself, (2) the signal from the detector, or (3) the high throughput HPLC software allows a facile manufacturing process when integrating different detectors.

Data acquisition from the UV (or other) detector(s) can be accomplished by storing the detector data into one file and extracting the detector data for each chromatogram after the chromatographic run. Alternatively, the detector data can be stored into separate chromatogram files as a function of time during the chromatographic run. Storing data into multiple files during the run is the preferred method since this will allow real-time display of each chromatogram in separate windows on the computer screen. Storing the data in a single file will preclude the display of individual chromatograms until after the run has ended. Thus, a preferred embodiment uses OEM detectors where detector data is available in real-time and developed software that allows a window to be displayed for each column. Complete specifications are always supplied on OEM equipment and thus the user has access to the detector data in real time for all detectors used (MS, UV-VIS, fluorescence, etc.). For example, Finnigan Inc. (San Jose, Calif.), is a major manufacturer of mass spectrometers. They produce a number of mass spectrometers that are appropriate for incorporation into a High Throughput LC/MS ($^{HT}$HPLC-MS) system. Their instruments include a many drivers, which allow their use in conjunction with some commercially available HPLC systems. A few of these drivers were developed in-house by Finnigan. However, many have been developed by external instrument companies such as Gilson and Beckman through a program called Virtual Instrument Partnership (VIP). Through this program, Finnigan supplies documentation and guidance in writing software that is able to: control instrument parameters, initiate data acquisition, and read the resulting data files from any of their mass spectrometers.

When this driver has been refined and meets all of Finnigan's requirements it is actually incorporated into the next release of their application software. This means that the off-the-shelf version of the software will immediately be able to use the accessory for which the driver was written. According to a contact at Finnigan, no accessory manufacturer has ever been turned down for inclusion in the VIP program.

Detector

The detection device coupled to the chromatographic system is a detector that produces signals/data that allow identification and quantification of detected compounds alone or in mixtures with other compounds. Exemplary of such detectors is a mass spectrometer, preferably run in a mild ionization mode such as electrospray ionization (ESI) or atmospheric pressure chemical ionization (APCI) and with either magnetic/electric sector or quadrupole rods as mass filters. Other examples of such detectors include those based on infrared or ultraviolet spectroscopy (e.g., FTIR or FTUV) and those based on nuclear magnetic resonance spectroscopy (NMR). Although FTUV technology does not exist yet, it is believed that quality research efforts over the past decades, aimed at developing such technology, have produced significant advances in this field to enable its implementation in the near future.

Examples of detectors other than mass spectrometers that are useful in the present invention are shown in Table 3.

TABLE 3

Detector models used to make High-Throughput HPLC instruments.

| Detector | Detector dead volume ($\mu L$) | Manufacturer |
|---|---|---|
| PDA | 3.2 | Varian |
| Fluorescence | 5 | Varian |
| Electrochemical | 1 | Varian |

Preferred UV detectors (and cell volumes) for use for the present invention include Chromtech (1 $\mu L$), Shimazdu (2.4 $\mu L$), HP (5 $\mu L$), Chromtech (10.5 $\mu L$), and Shimazdu (16 $\mu L$). Evaluating the chromatography as a function of switch rate and mobile phase volume for each of these detectors allows us to define the specifications of the 4 column eluent switch developed during preliminary testing.

Exemplary Components of the Present Invention

Examples of the components that can be utilized for building the high-throughput HPLC-UV ($^{HT}$HPLV-UV) instrument are given in Table 4.

TABLE 4

Components Used to Construct a High-Throughput HPLC-UV instrument.

| | |
|---|---|
| HP Kayak computer | Eldex pumps (9) |
| Computer control board (various) | Injectors (4) |
| Diaphragm valves (5) | Electronic controller |
| Stainless steel manifold | High pressure microsplitters (4) |
| Pneumatic solenoid valves (5) | |
| UV-VIS detector | |

Software useful for the present invention includes hardware-control-software (or just control-software) and data analysis software. Examples of tasks for control using software are given in Table 5.

TABLE 5

Software Tasks

| Control-software | Data analysis software |
|---|---|
| Variable flow rate pump control | Peak display from multiple columns |
| Binary system pump control | |
| Variable rate valve control | Mobile phase gradient display from multiple columns |
| Auto injector control | |
| Single-Channel UV/VIS detector data acquisition | Peak characterization (retention times, peak width, etc.) |
| Optimization of chromatogram display for a fixed wash cycle | Curve fitting for under sampled peaks |
| Software control of variable wash | |

Validation of the present invention was supported by the manufacturing of a prototype four-column $^{HT}$HPLC-UV system. The system was built according to the design depicted in FIG. 5, with in-line pH-meters and pressure sensors incorporated in the system. The $^{HT}$HPLC-UV is controlled by a dedicated PC through two interface boards. The user interface is programmed in the LabVIEW programming language. The computer system controls valve switching, injector actuation, and pump speed. It also acquires and logs data signals from the detector, pH meters and pressure sensors. All $^{HT}$HPLC operating parameters are user-configurable using the custom LabVIEW interface.

Hardware on the $^{HT}$THPLC system includes four injectors, and five diaphragm valves. All can be controlled either manually or under computer control through TTL signals. Manual control is through switches on the front panel of the $^{HT}$HPLC system. LED's on the front panel indicate the current state of each valve and indicator. The $^{HT}$HPLC system also includes four pressure sensors and four pH sensors, one for each column. Outputs from these devices are connected to eight panel meters with LED displays on the $^{HT}$HPLC front panel. Analog outputs from these panel meters are monitored by the control software and saved along with other $^{HT}$HPLC run data.

The five diaphragm valves (Valco Dv22-2116) each have two possible settings. In one setting they direct column flow into a six-port manifold (one port is blocked) and then to the detector. In the other setting they direct flow to waste. The detector is a single wavelength Varian model 340 UV/Vis detector. The output of the detector is monitored by the control software at a regular, user-selectable interval. After each run the data can be saved to disk by the user. LabVIEW© (National Instruments, Austin, Tex.) is a visual-programming environment that can be used to complete the tasks in Table 5. Boards installed in the computer can control external devices (pumps, injectors) and acquire data. Digital outputs can control the switch valves and injectors whereas analog outputs can control the pumps. Both analog and digital detector signals can be acquired using LabVIEW©. The data shown in FIG. 11B was generated using this instrument.

Applications

The present invention is generally directed to any chromatographic analysis method (HPLC, GC, CEC, microchips) that can be interfaced with a detector (MS, FTIR, FTUV, FTNMR) using an eluent switch system. As mentioned earlier, the major feature of the present invention is that it describes a technology that makes full (or better) use of the detector interfaced with the chromatographic system. Since the currently used detection techniques are usually quite expensive, the commercial advantage of the invention becomes evident: if the analytical capacity of the detector is increased several fold through the implementation of the proposed technology, it becomes more cost-efficient and is therefore worth a lot more valuable to the research/industrial fields where it has numerous applications.

One embodiment of the present invention is a multi-column HPLC/MS system, which is capable of processing the analysis of large numbers of compounds. One example of its application revolves around compound-dependent non-specific binding (as opposed to "specific binding") as a way to differentiate two or more compounds in a test solution. Specific binding is the affinity exhibited between a receptor molecule and a compound wherein the receptor molecule includes a defined binding locus that discriminatorily binds those compounds which have a predetermined chemical structure. Compounds not having the predetermined chemical structure do not bind with the binding site of the receptor molecule. "Compound-dependent non-specific binding" as used herein refers to that affinity interaction between a compound and a surface that does not have a specific discriminative binding locus for that compound, but rather the binding derives from the concomitant hydrophobic and/or hydrophilic interactions between the surface and the compound. Non-specific binding between a surface and a compound is "compound-dependent" in that, for any one surface, different compounds will interact and bind with such surface to varying degrees based upon the chemical structure and hydrophobic/hydrophilic nature of the compound. The high sensitivity of the MS detector allows the instantaneous identification of mixtures of compounds.

A mixture of 100 or more compounds can be injected simultaneously on several columns run in parallel and detected as they elute from the chromatographic system. In theory, depending on the loading capacity of the columns, a mixture of up to 1000 compounds can be analyzed simultaneously and in parallel on several chromatographic surfaces. The data from the MS analysis will be correlated to that of the UV detectors connected to each column, resulting in the assignment of a retention time and capacity factor for each and every compound detected. The data can be collected electronically and used as input for the calculation of one or more physicochemical values according to predetermined algorithms or equations.

In summary, the present invention can be applied to the rapid and efficient collection of databases of physicochemical values and/or biologically relevant parameters for large compound libraries. Consequently the present invention seems perfectly suited for lead identification and optimization of chemical libraries, which is a very important aspect of the drug discovery process, as well as QSAR studies. Once a "hit" compound has been identified, derivatization by the usual combinatorial chemistry tools to a large number of structurally similar parent molecules is possible. The present invention provides a convenient and efficient technique for the analysis of this pool of derivatives and the identification of one or more compounds with a data set of physicochemical values (derived from the chromatographic system) that would classify the compounds of interest as potential promising new leads.

Another broad field of application deals with high-throughput purification processes, such as those necessary in the drug discovery industry. By substituting preparative columns for analytical columns and interfacing the injection device with an autosampler and a 48-well, 96-well or other size parallel synthesis rack, by injecting the content of one well onto one column (one run with an n-column HPLC system would process n wells), one can conceive of a high-throughput parallel LC/MS purification technique similar to that designed by Kassel et al.; the main difference being our proposed post-column eluent switching device allowing us to independently monitor the chromatographic profile of each sample eluting from the parallel preparative columns. Also, the use of dedicated pumping systems for each column allows for the purification of chromatographically dissimilar compounds, that may require different types of columns (with differing packing material) and different mobile phase compositions.

An obvious example of application of the technique is separation conditions optimization. Since the system allows simultaneous injection of a sample mixture (the analyte) onto all columns run in parallel, elution of different mobile phase compositions on all columns if desired, and use of different types of columns (size and packing material), the system appears particularly well-suited for the study and optimization of separation conditions for any one mixture of compounds.

Other examples of useful applications are drug analysis/screening: evaluation of compounds put in contact with a surface suitable for pharmacokinetics and pharmacodynamics studies. The invention may also find applications in the field of diagnostics: physiological fluids sampling (such as blood or urine) for specific compounds that may be diagnostic of some disease or condition, or for metabolic studies, may be performed. The present invention may also be relevant to environmental sampling (water, soil analyses for contamination) and quality control in the food industry for example (e.g., flavors, ingredients, preservatives, etc.).

Other Embodiments of the Eluent Switch

Figure 14:
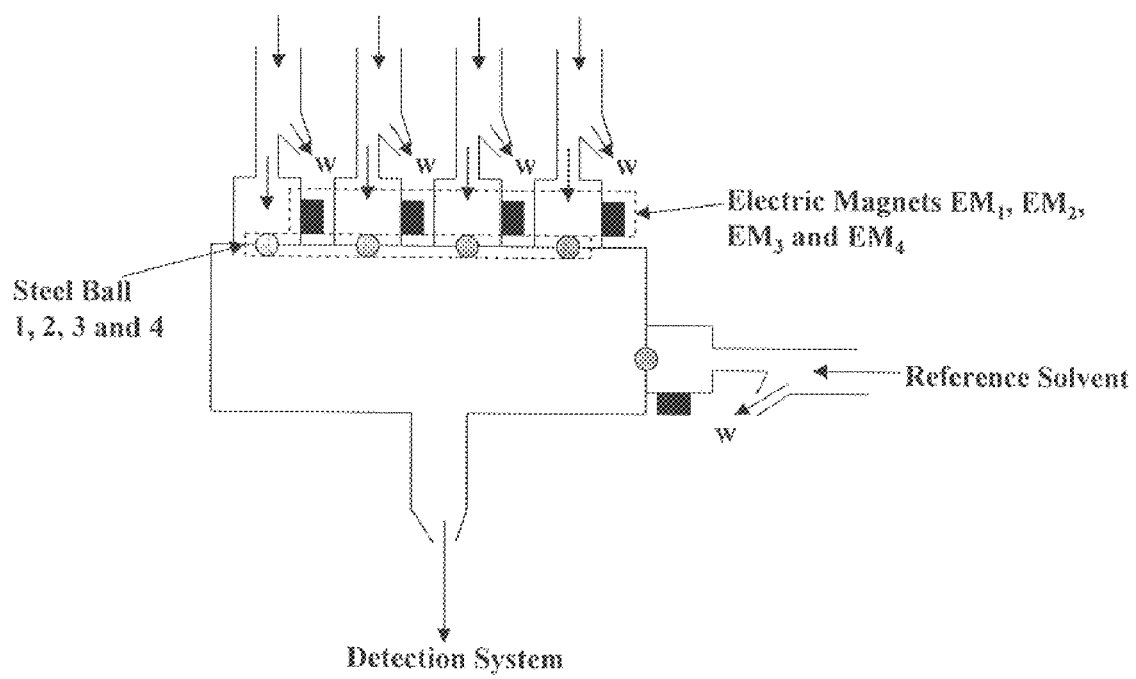
FIG. 14 depicts a design for the electromagnetically operated eluent switch system.
Figure 15:
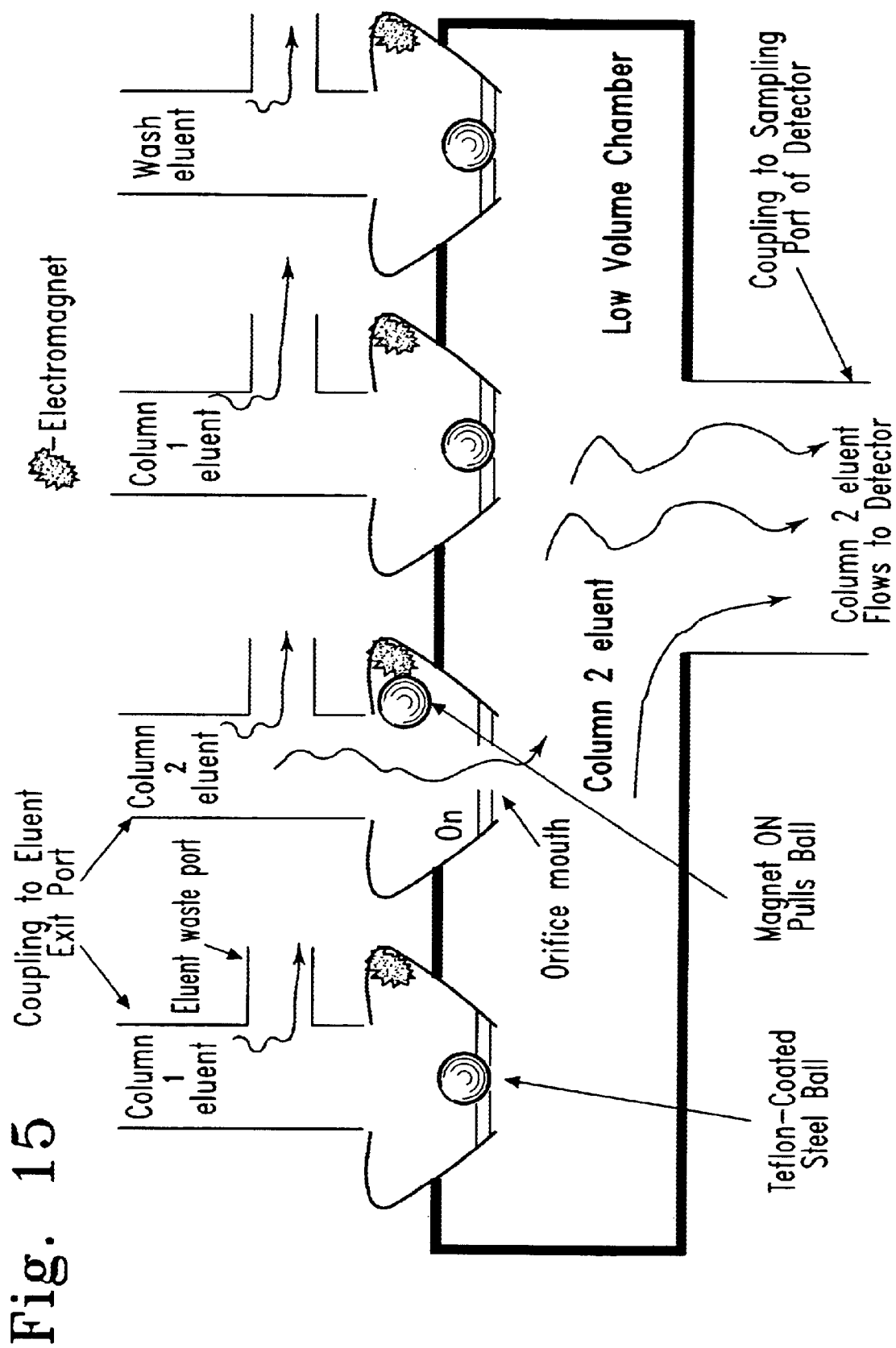
FIG. 15 details an embodiment of the electromechanical eluent switch.
Figure 16:
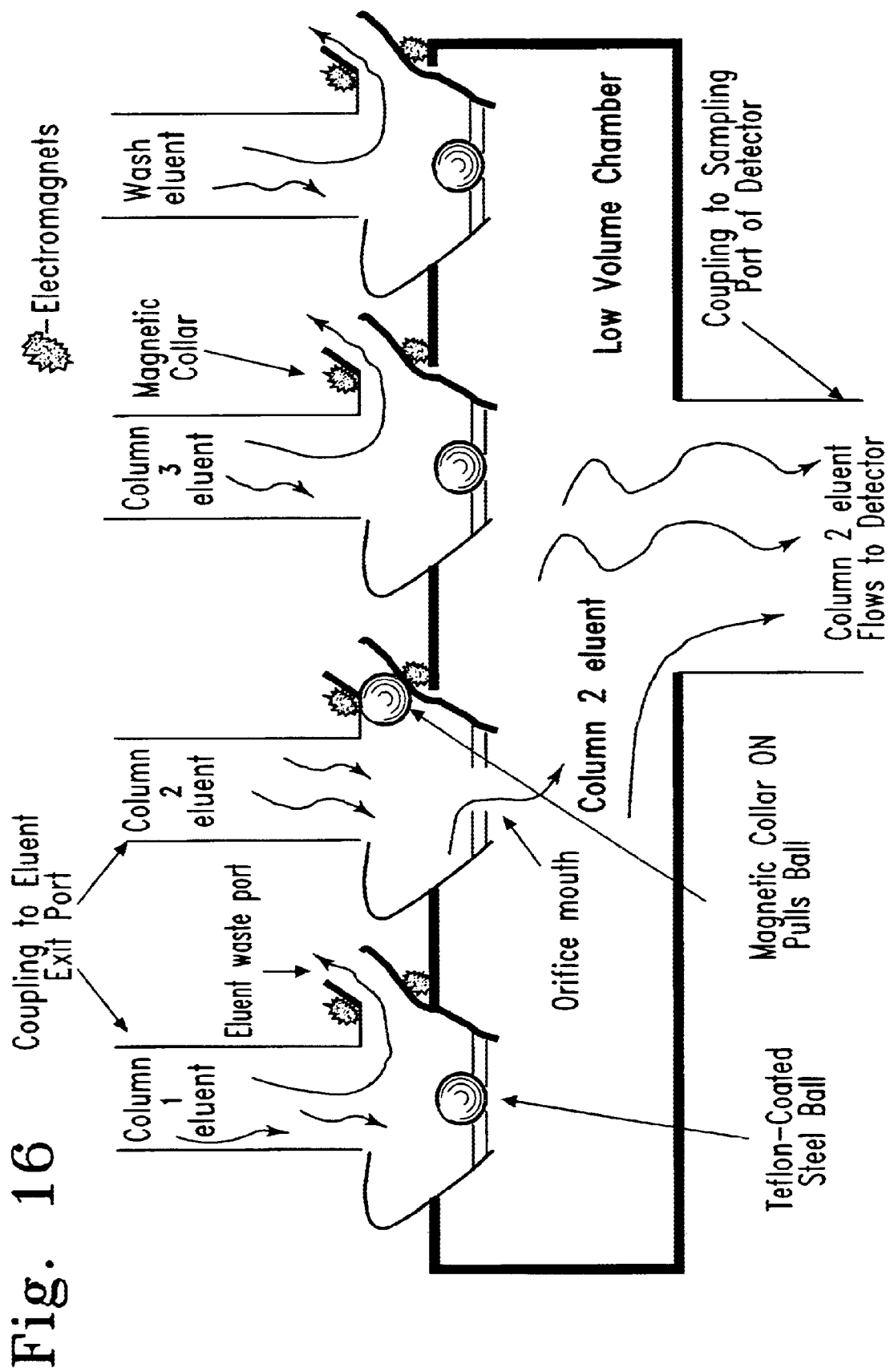
FIG. 16 details another embodiment of the electromechanical eluent switch.

The examples illustrated in FIGS. 14–16 require custom manufacturing of the eluent switch. The general concept is to have a magnetically induced switch to control the direction of solvent flow in each column to the detector. These figures illustrate potential methods of implementing the regulation of eluent flow by use of a magnetic switch.

As detailed in FIG. 14, one embodiment of the present invention relates to a modified version of the pre-detector chamber mentioned above whereby four individual compartments (three connected to the columns and the fourth connected to the reference solvent outlet) are mounted directly onto the chamber. Each compartment has an orifice through which the eluent accesses the main chamber. The opening/closing mechanism of the orifice can be accomplished by electromagnetic control of a steel ball (rubber or TEFLON coated) that fits perfectly in the groove of the compartment opening. Activation of the electric magnet removes the ball from the orifice mouth, thus allowing the eluent or wash solution to enter the main chamber. After the magnet is turned off, the steel ball is subjected to both gravity and eluent motion and will return and sit in the orifice cavity to close it. In a similar fashion as for the switch valves described above, the opening/closing of all four compartments can be controlled by computer software interfaced with the system to ensure the alternative delivery of the column eluents as well as the wash solution in the main chamber leading to the electrospray source housing, according to a predetermined sequence.

Two alternative embodiments of this design are illustrated in FIGS. 15 and 16. In FIG. 15, the eluent switch is configured with the eluent waste port located upstream (eluent flow-wise) from the steel ball and electomagnet such that, when the electromagnet is activated, the steel ball is moved out of the orifice mouth, thereby allowing eluent to flow into the low volume chamber without restricting eluent flow through the eluent waste port. From the low volume chamber, the eluent flows through a coupling to the sampling port of the detector. In this embodiment, the eluent waste port remains constantly open and at least a portion of the eluent from each respective column is constantly available for collection through the eluent waste port. In this configuration, the continuous collection of sample fractions is possible by using a fraction collector in eluent flow communication with the eluent waste port.

In FIG. 16, another embodiment is demonstrated. In this embodiment, the eluent switch is configured with the eluent waste port located in close proximity to the electromagnets, which optionally are configured to form a magnetic collar surrounding the eluent waste port. In this configuration, activation of the electromagnets results in movement of the steel ball away from the orifice mouth, thus allowing eluent to flow into the low volume chamber, while simultaneously obstructing eluent flow by blocking the eluent waste port. In this embodiment, flow of eluent from each respective column is directed either into the low volume chamber or through the eluent waste port. This embodiment allows delivery of sample portions to the detector without generating waste eluent or losing any unnecessary sample through the eluent waste port. The collection of sample fractions is possible by using a fraction collector in eluent flow communication with the eluent waste port.

FIGS. 15 and 16 demonstrate embodiments readily adaptable to control by electronic control devices, such as (but not limited to) computers with software. For example, the embodiment in FIG. 16 is readily adapted to allow a computer to control the sequence and duration in which the electromagnets are activated, thus controlling the sequence and volume of sample from each respective column delivered to the detector. In one optional variation of this embodiment, the eluent switch is in electronic communication with a computer programmed to deliver signals which activate the electromagnets and thereby allow portions of eluent to flow from each of the respective columns and/or wash eluent into the low volume chamber in the following order: Column 1; Wash Eluent, Column 2; Wash Eluent; Column Three; Wash Eluent. Further, the computer is programmed such that this sequence continually repeats during a predetermined time spanning the course of the elution of sample compounds.

The embodiments of the eluent switch listed above are not intended as an exclusive list of the embodiments within the scope of the present invention. It is intended that the invention not be limited by virtue of the recitation of the previous embodiments, but instead that these embodiments be considered but illustrative of the scope of the invention. Variations of such embodiments and their equivalents will be readily apparent to those of ordinary skill in the art.

What is claimed is:

1. A method for data acquisition by analysis of eluent streams from multiple chromatographic columns in a chromatographic system using an eluent stream analyzer having a fluid sampling port and capable of providing signals characteristic of detected chemical species in each eluent stream, said method comprising
   providing a chromatoraphic system with multiple chromatograthic columns, each having an eluent stream, and an eluent switching valve having
   (1) fluid input ports in fluid communication with the eluent stream from each chromatographic column and with a source of at least one indexing fluid,
   (2) a fluid output port in fluid flow communication with a fluid sampling port on the eluent stream analyzer, and
   (3) a valve system communicating with a programmable controller for directing aliquots of the respective eluent streams and indexing fluid in a programmed sequence through the fluid output port and toward the fluid sampling port on the eluent stream analyzer,
   directing the aliquots via the valve system to the eluent stream analyzer and producing signals characteristic of detected chemical species in each aliquot, and
   correlating the electronic storage of the signals from the analyzer with the programmed sequence so that analyzer signals from analysis of the aliquots of eluent of each respective column are stored in an algorithm accessible electronic storage device.

2. The method of claim 1 wherein the correlating step includes sensing aliquots of indexing fluid between each eluent stream aliquot.

3. The method of claim 1 wherein the indexing fluid comprises a liquid.

4. The method of claim 3 wherein the liquid comprises at least one analyzer detectable species.

5. The method of claim 1 wherein the indexing fluid comprises a gas.

6. The method of claim 1 wherein the indexing fluid comprises a liquid and a gas.

7. The method of claim 1 wherein the chromatographic system further comprises a pump for controlling pressure or a valve for controlling rate of flow of the respective eluent streams and indexing fluid through the valve system and toward the fluid sampling port on the eluent stream analyzer.

8. The method of claim 1 wherein the respective aliquots of indexing fluid between aliquots of the respective eluent streams are of programmably unique volumes.

9. The method of claim 1 wherein the controller for the valve system is programmed to deliver at least one aliquot of indexing fluid through the output port after each eluent stream aliquot.

10. The method of claim 1 wherein the analyzer senses the respective indexing fluid aliquots and directs the signals from the next following eluent stream aliquot to a predetermined electronic data storage register where eluent aliquot analysis signals for each respective chromatographic column is stored in an accessible format.

11. The method of claim 1 wherein the chromatographic system further comprises a flow rate detector and a flow rate controller for each chromatographic column.

12. A multi-column chromatographic system comprising
   at least two chromatographic columns each having a mobile phase input port and an eluent stream output port;
   a mobile phase delivery system in fluid flow communication with each the mobile phase input port;
   an eluent stream analyzer having a fluid sampling port and capable of providing signals characteristic of chemical species in a fluid received in said sampling port;
   an eluent switching valve assembly having
   (1) a fluid input port positioned for fluid communication with the eluent stream from each chromatographic column and with a source of at least one indexing fluid,
   (2) a fluid output port in fluid flow communication with the fluid sampling port of the eluent stream analyzer; and
   (3) a valve system for directing aliquot volumes of the respective eluent streams and the indexing fluid in a programmed sequence through the fluid output port and toward the fluid sampling port on the eluent stream analyzer;
   an electronic data storage device for receiving and storing signals from the eluent stream analyzer representative of analysis of eluent stream aliquots of each respective chromatographic column; and
   a programmable controller (computer) including an algorithm including instructions for sensing the presence, volume or components of an indexing fluid aliquot at the fluid sampling port of the analyzer and directing signals from the analyzer for eluent stream aliquots corresponding to the respective chromatographic columns to electronic data storage registers/devices designated for data storage for the respective chromatographic columns.

13. The multi-column chromatographic system of claim 12 wherein the fluid input port on the eluent switching valve assembly is positioned for fluid communication with the eluent stream from each chromatographic column and with a pressure control source of at least one indexing liquid and at least one indexing gas.

14. The multi-column chromatographic system of claim 12 wherein the eluent stream analyzer comprises a mass spectrometer.

15. The multi-column chromatographic system of claim 12 wherein the eluent stream analyzer comprises an infra-red spectrometer.

16. The multi-column chromatographic system of claim 12 wherein the eluent stream analyzer comprises a nuclear magnetic resonance spectrometer.

17. The multi-column chromatographic system of claim 12 wherein the eluent stream analyzer comprises an ultraviolet-visible spectrometer.

18. The multi-column chromatographic system of claim 12 wherein the eluent stream analyzer is selected from the group consisting of a fluorescence detector, an electrochemical detector and a refractive index detector.

19. The method of claim 1 wherein the eluent stream analyzer is selected from the group consisting of a mass spectrometer, an infra-red spectrometer, a nuclear magnetic resonance spectrometer, an ultraviolet-visible spectrometer, a fluorescence detector, an electrochemical detector and a refractive index detector.

20. The method of claim 1 wherein the signal from the analyzer is used as "feed back" signal to control the programmable controller.

21. The multi-column chromatographic system of claim 12 wherein the signal from the analyzer is used as "feed back" signal to control the programmable controller.

* * * * *